(12) United States Patent
Falo, Jr. et al.

(10) Patent No.: US 9,944,019 B2
(45) Date of Patent: Apr. 17, 2018

(54) TIP-LOADED MICRONEEDLE ARRAYS FOR TRANSDERMAL INSERTION

(71) Applicants: University of Pittsburgh—Of the Commonwealth System of Higher Education, Pittsburgh, PA (US); Carnegie Mellon University, Pittsburgh, PA (US)

(72) Inventors: Louis D. Falo, Jr., Wexford, PA (US); Geza Erdos, Wexford, PA (US); O. Burak Ozdoganlar, Sewickley, PA (US)

(73) Assignees: University of Pittsburgh—Of the Commonwealth System of Higher Education, Pittsburgh, PA (US); Carnegie Mellon University, Pittsburgh, PA (US)

( * ) Notice: Subject to any disclaimer, the term of this patent is extended or adjusted under 35 U.S.C. 154(b) by 62 days.

(21) Appl. No.: 14/398,375

(22) PCT Filed: May 1, 2013

(86) PCT No.: PCT/US2013/039084
§ 371 (c)(1),
(2) Date: Oct. 31, 2014

(87) PCT Pub. No.: WO2013/166162
PCT Pub. Date: Nov. 7, 2013

(65) Prior Publication Data
US 2015/0126923 A1    May 7, 2015

Related U.S. Application Data

(60) Provisional application No. 61/641,209, filed on May 1, 2012.

(51) Int. Cl.
*B29C 67/00* (2017.01)
*A61K 9/00* (2006.01)
(Continued)

(52) U.S. Cl.
CPC ............ *B29C 67/00* (2013.01); *A61K 9/0021* (2013.01); *A61L 31/042* (2013.01); *A61L 31/16* (2013.01);
(Continued)

(58) Field of Classification Search
CPC ........ A61K 9/0021; A61M 2037/0046; A61M 2037/0053; A61M 37/0015; B23C 3/20; B29L 2031/7544
See application file for complete search history.

(56) References Cited

U.S. PATENT DOCUMENTS

| | | |
|---|---|---|
| 5,658,515 A | 8/1997 | Lee et al. |
| 6,331,266 B1 | 12/2001 | Powell et al. |

(Continued)

FOREIGN PATENT DOCUMENTS

| | | |
|---|---|---|
| CN | 1479590 A | 3/2004 |
| JP | 2005-35945 | 2/2005 |

(Continued)

OTHER PUBLICATIONS

International Search Report and Written Opinion dated Jan. 14, 2016 by the Australian Patent Office, acting as ISA for PCT App. No. PCT/US2015/059556, 11 pages.

(Continued)

*Primary Examiner* — Quynh-Nhu H Vu
(74) *Attorney, Agent, or Firm* — Klarquist Sparkman, LLP

(57) ABSTRACT

A method of forming a microneedle array can include forming a microneedle array that has one or more bioactive component. The microneedle array can include a base por-
(Continued)

tion and plurality of microneedles extending from the base portion, and the one or more bioactive components are present in a higher concentration in the plurality of microneedles than in the base portion.

14 Claims, 21 Drawing Sheets

(51) Int. Cl.
    *A61L 31/16*     (2006.01)
    *A61M 37/00*     (2006.01)
    *A61L 31/04*     (2006.01)
    *B23C 3/20*     (2006.01)
    *B29L 31/00*     (2006.01)
    *A61B 17/00*     (2006.01)

(52) U.S. Cl.
    CPC .......... *A61M 37/0015* (2013.01); *B23C 3/20* (2013.01); *A61B 2017/00526* (2013.01); *A61L 2300/802* (2013.01); *A61L 2400/18* (2013.01); *A61M 2037/0046* (2013.01); *A61M 2037/0053* (2013.01); *B29L 2031/7544* (2013.01)

(56) References Cited

U.S. PATENT DOCUMENTS

| | | |
|---|---|---|
| 6,451,240 B1 | 9/2002 | Sherman et al. |
| 6,511,463 B1 | 1/2003 | Wood et al. |
| 6,565,871 B2 | 5/2003 | Roser et al. |
| 6,611,707 B1 | 8/2003 | Prausnitz et al. |
| 6,623,707 B1 | 9/2003 | Addiego et al. |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,743,211 B1 | 6/2004 | Prausnitz et al. |
| 6,767,211 B2 | 7/2004 | Hall et al. |
| 6,881,203 B2 | 4/2005 | Delmore et al. |
| 6,899,838 B2 | 5/2005 | Lastovich |
| 6,908,453 B2 | 6/2005 | Fleming et al. |
| 6,924,087 B2 | 8/2005 | Yeshurun et al. |
| 6,931,277 B1 | 8/2005 | Yuzhakov et al. |
| 7,052,268 B2 | 5/2006 | Powell et al. |
| 7,132,054 B1 | 11/2006 | Kravitz et al. |
| 7,211,062 B2 | 5/2007 | Kwon |
| 7,226,439 B2 | 6/2007 | Prausnitz et al. |
| 7,285,113 B2 | 10/2007 | Yeshurun |
| 7,315,758 B2 | 1/2008 | Kwiatkowski et al. |
| 7,316,665 B2 | 1/2008 | Laurent et al. |
| 7,332,197 B2 | 2/2008 | Wood et al. |
| 7,364,568 B2 | 4/2008 | Angel et al. |
| 7,416,541 B2 | 8/2008 | Yuzhakov et al. |
| 7,429,333 B2 | 9/2008 | Chiou et al. |
| 7,497,980 B2 | 3/2009 | Xu et al. |
| 7,560,036 B2 | 7/2009 | Golubovic-Liakopoulos et al. |
| 7,578,954 B2 | 8/2009 | Gartstein et al. |
| 7,588,552 B2 | 9/2009 | Yeshurun et al. |
| 7,591,806 B2 | 9/2009 | Xu |
| 7,648,484 B2 | 1/2010 | Yeshurun et al. |
| 7,651,475 B2 | 1/2010 | Angel et al. |
| 7,658,728 B2 | 2/2010 | Yuzhakov |
| 7,699,819 B2 | 4/2010 | Yeung et al. |
| 7,731,968 B2 | 6/2010 | Mikszta et al. |
| D619,245 S | 7/2010 | Moga et al. |
| 7,753,888 B2 | 7/2010 | Mukerjee et al. |
| 7,763,203 B2 | 7/2010 | Arias et al. |
| 7,785,301 B2 | 8/2010 | Yuzhakov |
| 7,846,488 B2 | 12/2010 | Johnson et al. |
| 7,850,657 B2 | 12/2010 | Yeshurun et al. |
| D638,534 S | 5/2011 | Moga et al. |
| 8,052,633 B2 | 11/2011 | Kendall |
| 8,057,842 B2 | 11/2011 | Choi et al. |
| 8,062,573 B2 | 11/2011 | Kwon |
| 8,062,835 B2 | 11/2011 | Tomono |
| 8,088,321 B2 | 1/2012 | Ferguson et al. |
| 8,101,114 B2* | 1/2012 | Park .................. A61M 37/0015 264/442 |
| 8,137,736 B2 | 3/2012 | Zhu et al. |
| 8,162,901 B2 | 4/2012 | Gonnelli et al. |
| 8,167,852 B2 | 5/2012 | Quan et al. |
| 8,172,815 B2 | 5/2012 | Down et al. |
| 8,192,787 B2 | 6/2012 | Kirby |
| 8,216,190 B2 | 7/2012 | Gartstein et al. |
| 8,236,368 B2 | 8/2012 | Jung et al. |
| 8,246,582 B2 | 8/2012 | Angel et al. |
| 8,246,893 B2 | 8/2012 | Ferguson et al. |
| 8,250,729 B2 | 8/2012 | Lee et al. |
| 8,257,324 B2 | 9/2012 | Prausnitz et al. |
| 8,267,889 B2 | 9/2012 | Cantor et al. |
| 8,328,757 B2 | 12/2012 | Beebe et al. |
| 8,353,861 B2 | 1/2013 | Tobinaga et al. |
| 8,354,033 B2 | 1/2013 | Scholten et al. |
| 8,361,037 B2 | 1/2013 | Gonnelli |
| 8,366,677 B2 | 2/2013 | Kaspar et al. |
| 8,376,984 B2 | 2/2013 | James |
| 8,402,629 B2 | 3/2013 | Lee et al. |
| 8,414,548 B2 | 4/2013 | Yuzhakov |
| 8,414,959 B2 | 4/2013 | Hye-Ok et al. |
| 8,419,708 B2 | 4/2013 | Tokumoto et al. |
| 8,444,622 B2 | 5/2013 | Eckhoff et al. |
| 8,449,807 B2 | 5/2013 | Ferguson et al. |
| 8,454,844 B2 | 6/2013 | Yeshurun et al. |
| 8,491,534 B2 | 7/2013 | Takada |
| 8,506,530 B2 | 8/2013 | Laermer et al. |
| 8,506,980 B2 | 8/2013 | Takada |
| 8,545,741 B2 | 10/2013 | Jung et al. |
| 8,551,391 B2 | 10/2013 | Chang et al. |
| 8,554,317 B2 | 10/2013 | Duan |
| 8,560,059 B2 | 10/2013 | Hoarau et al. |
| 8,579,862 B2 | 11/2013 | Kobayashi et al. |
| 8,603,384 B2 | 12/2013 | Luttge et al. |
| 8,636,696 B2 | 1/2014 | Ross et al. |
| 8,637,136 B2 | 1/2014 | Ferguson et al. |
| 8,671,544 B2 | 3/2014 | Xu et al. |
| 8,696,637 B2 | 4/2014 | Ross |
| 8,696,638 B2 | 4/2014 | Terahara et al. |
| 8,708,966 B2 | 4/2014 | Allen et al. |
| 8,734,697 B2 | 5/2014 | Chen et al. |
| 8,741,377 B2 | 6/2014 | Choi et al. |
| 8,747,362 B2 | 6/2014 | Terahara et al. |
| 8,758,298 B2 | 6/2014 | Cantor et al. |
| 8,771,781 B2 | 7/2014 | Tokumoto et al. |
| 8,784,368 B2 | 7/2014 | Eckhoff et al. |
| 8,784,373 B2 | 7/2014 | Gharib et al. |
| 8,784,383 B2 | 7/2014 | Cole et al. |
| 8,784,384 B2 | 7/2014 | Boyden et al. |
| 8,784,385 B2 | 7/2014 | Boyden et al. |
| 8,784,860 B2 | 7/2014 | Falotico et al. |
| 8,785,400 B2 | 7/2014 | Levetan et al. |
| 8,788,037 B2 | 7/2014 | Della Rocca et al. |
| 8,788,211 B2 | 7/2014 | Boyden et al. |
| 8,788,212 B2 | 7/2014 | Boyden et al. |
| 8,790,257 B2 | 7/2014 | Libbus et al. |
| 8,790,259 B2 | 7/2014 | Katra et al. |
| 8,790,658 B2 | 7/2014 | Cigarini et al. |
| 8,791,062 B2 | 7/2014 | Hsu et al. |
| 8,791,107 B2 | 7/2014 | Chang et al. |
| 8,793,075 B2 | 8/2014 | Boyden et al. |
| 8,795,174 B2 | 8/2014 | Manicka et al. |
| 8,795,201 B2 | 8/2014 | Escutia et al. |
| 8,795,230 B2 | 8/2014 | Schoonmaker et al. |
| 8,795,234 B2 | 8/2014 | Kadamus et al. |
| 8,795,259 B2 | 8/2014 | Beebe et al. |
| 8,796,436 B2 | 8/2014 | Manoharan et al. |
| 8,798,722 B2 | 8/2014 | Rylander et al. |
| 8,798,932 B2 | 8/2014 | Boyden et al. |
| 8,798,933 B2 | 8/2014 | Boyden et al. |
| 8,821,446 B2 | 9/2014 | Trautman et al. |
| 8,821,779 B2 | 9/2014 | Ferguson et al. |
| 8,834,423 B2 | 9/2014 | Falo, Jr. |
| 2002/0082543 A1* | 6/2002 | Park .................. A61B 5/1411 604/21 |

(56) References Cited

U.S. PATENT DOCUMENTS

| | | | |
|---|---|---|---|
| 2002/0193729 A1* | 12/2002 | Cormier | A61B 17/205 604/272 |
| 2002/0198509 A1 | 12/2002 | Mikszta et al. | |
| 2004/0058882 A1 | 3/2004 | Eriksson et al. | |
| 2005/0049549 A1* | 3/2005 | Wong | A61B 10/0064 604/46 |
| 2005/0065463 A1 | 3/2005 | Tobinaga et al. | |
| 2005/0089553 A1 | 4/2005 | Cormier et al. | |
| 2005/0251088 A1* | 11/2005 | Kwon | A61M 37/0015 604/60 |
| 2007/0161964 A1 | 7/2007 | Yuzhakov | |
| 2007/0260201 A1* | 11/2007 | Prausnitz | A61F 9/0017 604/272 |
| 2008/0009763 A1 | 1/2008 | Chiou et al. | |
| 2008/0208134 A1 | 8/2008 | Tomono | |
| 2008/0213461 A1 | 9/2008 | Gill et al. | |
| 2008/0221532 A1 | 9/2008 | Ogawa | |
| 2008/0269685 A1* | 10/2008 | Singh | A61K 9/0021 604/173 |
| 2009/0054842 A1* | 2/2009 | Yeshurun | A61M 37/0015 604/173 |
| 2010/0042137 A1* | 2/2010 | Oronsky | A61M 37/0015 606/204 |
| 2010/0228203 A1 | 9/2010 | Quan et al. | |
| 2011/0046575 A1* | 2/2011 | Takada | A61K 9/0021 604/265 |
| 2011/0098651 A1* | 4/2011 | Falo, Jr. | A61M 37/0015 604/173 |
| 2011/0172605 A1* | 7/2011 | Berenschot | A61M 37/0015 604/173 |
| 2011/0230736 A1 | 9/2011 | Tepper et al. | |
| 2012/0078189 A1 | 3/2012 | Ogawa et al. | |
| 2012/0123341 A1* | 5/2012 | Birchall | A61K 9/0021 604/173 |
| 2012/0265145 A1* | 10/2012 | Mefti | A61M 37/0015 604/173 |
| 2013/0072902 A1* | 3/2013 | Takada | A61M 37/0015 604/506 |
| 2014/0066843 A1* | 3/2014 | Zhang | A61K 9/0021 604/46 |
| 2014/0142541 A1 | 5/2014 | Yan et al. | |
| 2015/0030642 A1* | 1/2015 | Wu | A61K 9/0021 424/400 |

FOREIGN PATENT DOCUMENTS

| | | |
|---|---|---|
| JP | 2011-224332 | 11/2011 |
| WO | WO 2009-004995 | 1/2009 |
| WO | WO 2009/009004 | 1/2009 |
| WO | WO 2009/040548 | 4/2009 |
| WO | WO 2009/081122 | 7/2009 |
| WO | WO 2010/022252 | 2/2010 |
| WO | WO 2010/071918 | 7/2010 |
| WO | WO 2010/141377 | 12/2010 |
| WO | WO 2012/054582 | 4/2012 |
| WO | WO 2012/153266 | 11/2012 |
| WO | WO 2013/166162 | 11/2013 |

OTHER PUBLICATIONS

European Search Report dated Mar. 10, 2016 by the European Patent Office, for EPC App. No. 13784192.0, 14 pages.

Office Action, dated Sep. 14, 2017, for corresponding Japanese Patent Application No. 2015-510434, no English-language translation, 4 pages.

Office Action, dated Oct. 31, 2017, in corresponding Chinese Patent Application No. 201380031604.6, with English-language translation, 18 pages.

* cited by examiner

FIG. 5A
FIG. 5B
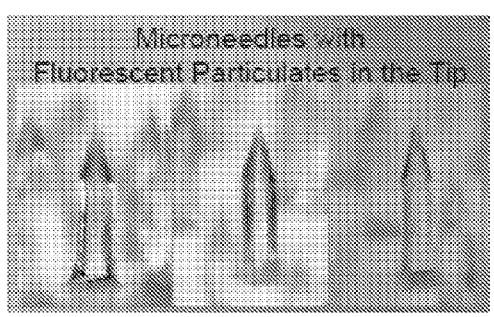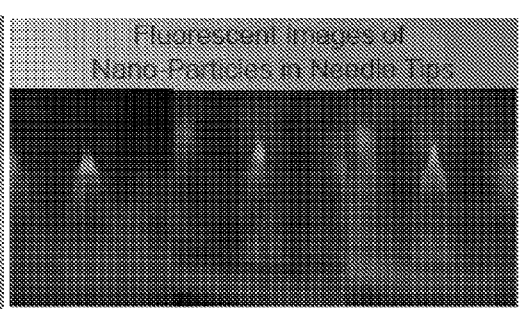
FIG. 6A
FIG. 6B
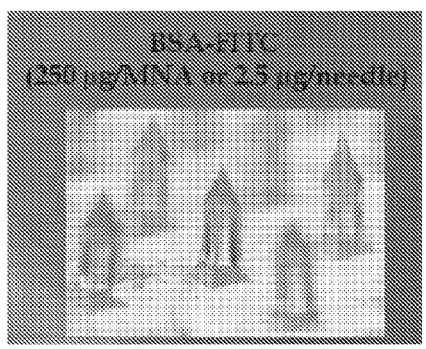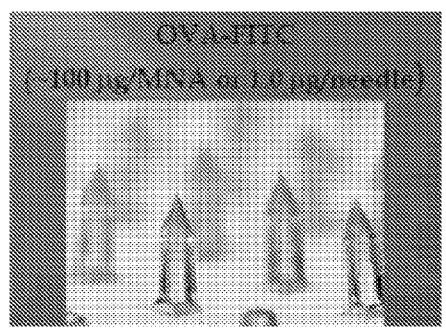

FIG. 11A  FIG. 11B  FIG. 11C  FIG. 11D
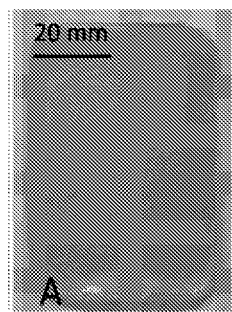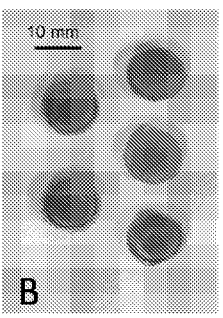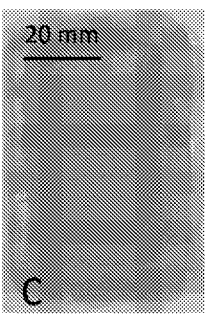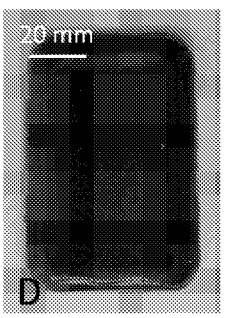
FIG. 12A  FIG. 12B
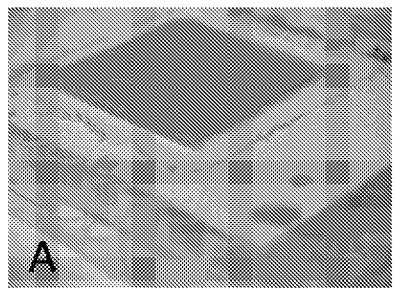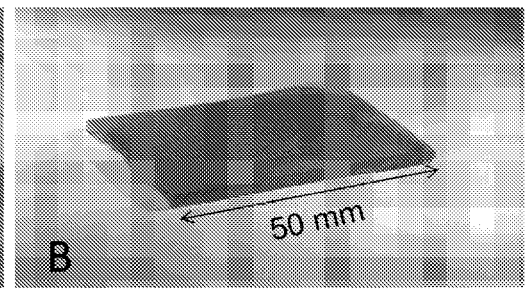

FIG. 15
Cross-section of the CMC-solid with layers of active components and interleaving CMC layers
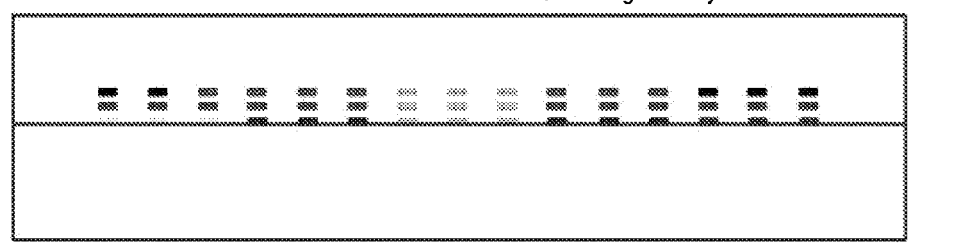
Cross-section of finished MNA-device after the micro-milling process
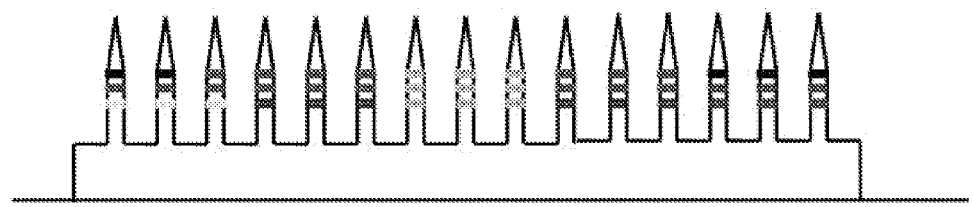

FIG. 25A    FIG. 25B    FIG. 25C
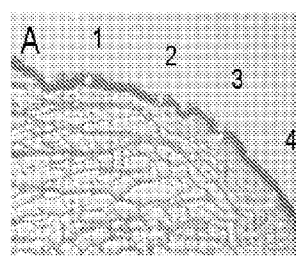  
FIG. 26A          FIG. 26B
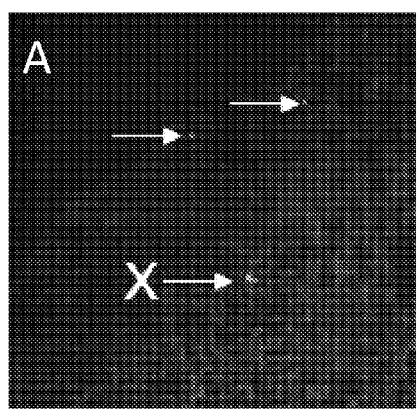 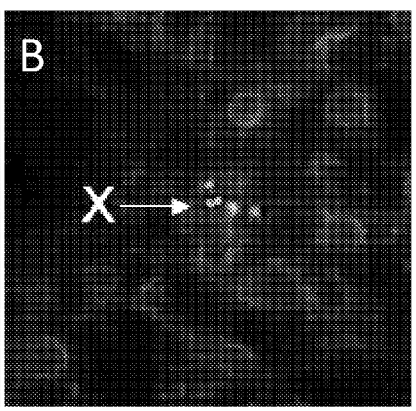
FIG. 27
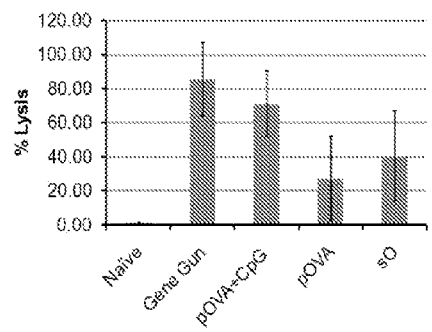

FIG. 28
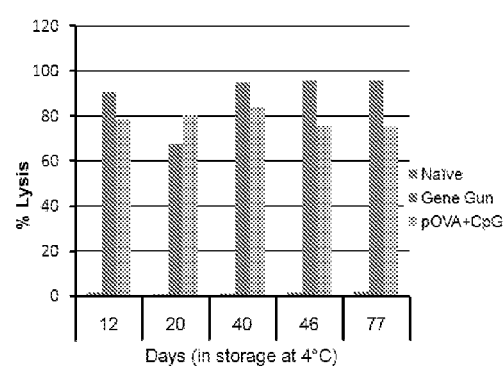
FIG. 29A     FIG. 29B
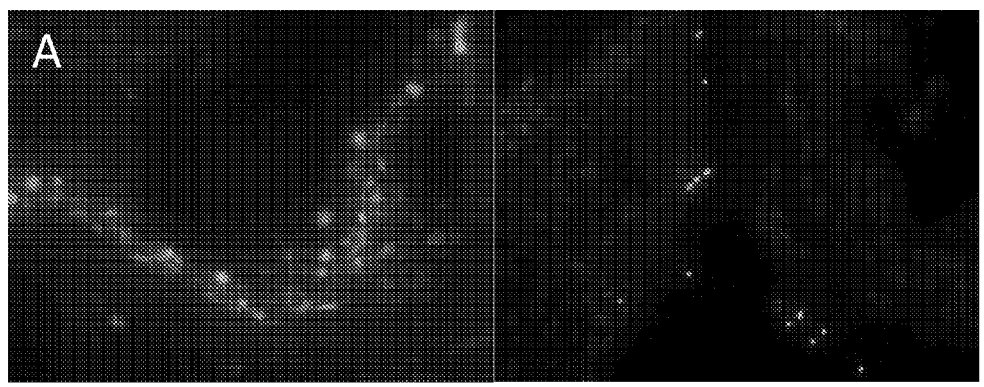

FIG. 30
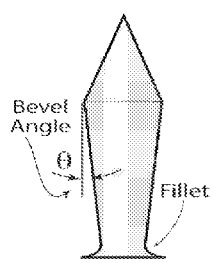
FIG. 31                    FIG. 32
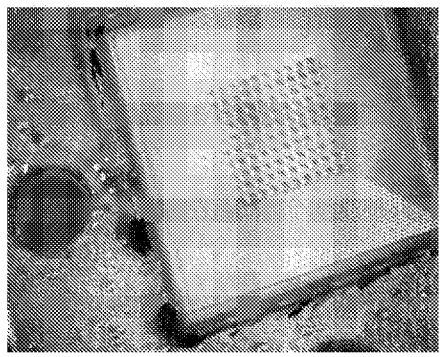 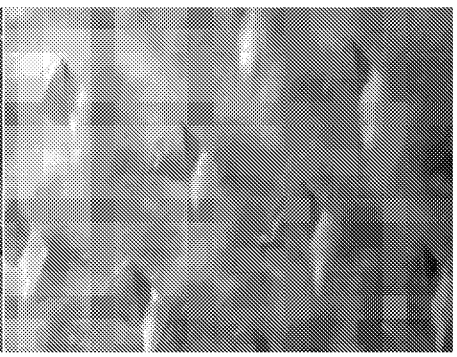

HFO-Applicator for Laboratory and Clinical Insertion of MNAs

TIP-LOADED MICRONEEDLE ARRAYS FOR TRANSDERMAL INSERTION

RELATED APPLICATIONS

This is the U.S. National Stage of International Application No. PCT/US2013/039084, filed May 1, 2013, which was published in English under PCT Article 21(2), which in turn claims the benefit of U.S. Provisional Application No. 61/641,209, filed May 1, 2012. The provisional application is incorporated by reference herein in its entirety.

ACKNOWLEDGMENT OF GOVERNMENT SUPPORT

This invention was made with government support under grant numbers EB012776, AI076060, and CA121973 awarded by the National Institutes of Health. The government has certain rights in the invention.

FIELD

The disclosure pertains to systems and methods for transdermal drug delivery, and, in particular, to systems and methods for making and using dissolvable microneedle arrays.

BACKGROUND

The remarkable physical barrier function of the skin poses a significant challenge to transdermal drug delivery. To address this challenge, a variety of microneedle-array based drug delivery devices have been developed. For example, one conventional method employs solid or hollow microneedles arrays with no active component. Such microneedle arrays can pre-condition the skin by piercing the stratum corneum and the upper layer of epidermis to enhance percutaneous drug penetration prior to topical application of a biologic-carrier or a traditional patch. This method has been shown to significantly increase the skin's permeability; however, this method provides only limited ability to control the dosage and quantity of delivered drugs or vaccine.

Another conventional method uses solid microneedles that are surface-coated with a drug. Although this method provides somewhat better dosage control, it greatly limits the quantity of drug delivered. This shortcoming has limited the widespread application of this approach and precludes, for example, the simultaneous delivery of optimal quantities of combinations of antigens and/or adjuvant in vaccine applications.

Another conventional method involves using hollow microneedles attached to a reservoir of biologics. The syringe needle-type characteristics of these arrays can significantly increase the speed and precision of delivery, as well as the quantity of the delivered cargo. However, complex fabrication procedures and specialized application settings limit the applicability of such reservoir-based microneedle arrays.

Yet another conventional method involves using solid microneedle arrays that are biodegradable and dissolvable. Current fabrication approaches for dissolvable polymer-based microneedles generally use microcasting processes. However, such conventional processes are limited in the active components that can be embedded into the array and are also wasteful in that they require that the active components be homogenously embedded in the microneedles and their support structures.

Accordingly, although transdermal delivery of biologics using microneedle-array based devices offers attractive theoretical advantages over prevailing oral and needle-based drug delivery methods, considerable practical limitations exist in the design and fabrication associated with microneedle arrays constructed using conventional processes.

SUMMARY

The systems and methods disclosed herein include cutaneous delivery platforms based on dissolvable microneedle arrays that can provide efficient, precise, and reproducible delivery of biologically active molecules to human skin. The microneedle array delivery platforms can be used to deliver a broad range of bioactive components to a patient.

The foregoing and other objects, features, and advantages of the disclosed embodiments will become more apparent from the following detailed description, which proceeds with reference to the accompanying figures.

BRIEF DESCRIPTION OF THE DRAWINGS

FIGS. 5A and 5B illustrate exemplary microneedles with tip-loaded active components.

FIGS. 6A and 6B illustrate exemplary microneedles with tip-loaded active components.

FIGS. 11A-11D illustrate exemplary CMC-solids and embedded active components.

FIGS. 12A-12B illustrate exemplary CMC-solids and embedded active components.

FIG. 15 is a schematic illustration of exemplary microneedle arrays fabricated in a spatially controlled manner.

FIGS. 25A, 25B, and 25C illustrate the effectiveness of microneedle arrays in penetrating skin explants.

FIGS. 26A and 26B illustrate in vivo delivery of particulates to the skin draining lymph nodes of microneedle array immunized mice.

FIG. 27 is a bar graph showing immunogenicity of microneedle delivered model antigens.

FIG. 28 is a bar graph showing the stability of the active cargo of CMC-microneedle arrays in storage.

FIGS. 29A and 29B show induction of apoptosis in epidermal cells that have been delivered Cytoxan® (cyclophosphamide) through a microneedle array.

FIG. 30 illustrates a microneedle geometry that can be formed by direct micromilling of a block of material.

FIG. 31 is a stereo microscopic image of a direct-fabricated solid CMC-microneedle array.

FIG. 32 is a stereo microscopic image of a portion of the microneedle array of FIG. 31.

DETAILED DESCRIPTION

Figure 1:
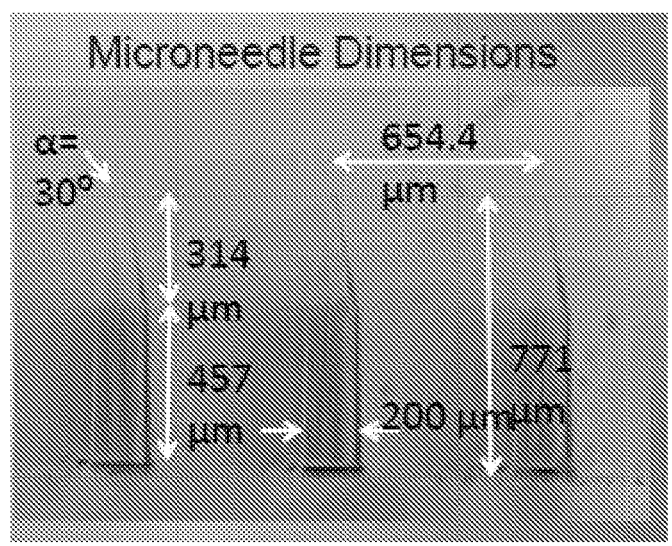
FIG. 1 illustrates exemplary microneedles and their dimensions.

The following description is exemplary in nature and is not intended to limit the scope, applicability, or configuration of the disclosed embodiments in any way. Various changes to the described embodiment may be made in the function and arrangement of the elements described herein without departing from the scope of the disclosure.

As used in this application and in the claims, the singular forms "a," "an," and "the" include the plural forms unless the context clearly dictates otherwise. Additionally, the term "includes" means "comprises." As used herein, the terms "biologic," "active component," "bioactive component," "bioactive material," or "cargo" refer to pharmaceutically active agents, such as analgesic agents, anesthetic agents, anti-asthmatic agents, antibiotics, anti-depressant agents, anti-diabetic agents, anti-fungal agents, anti-hypertensive agents, anti-inflammatory agents, anti-neoplastic agents, anxiolytic agents, enzymatically active agents, nucleic acid constructs, immunostimulating agents, immunosuppressive agents, vaccines, and the like. The bioactive material can comprise dissoluble materials, insoluble but dispersible materials, natural or formulated macro, micro and nano particulates, and/or mixtures of two or more of dissoluble, dispersible insoluble materials and natural and/or formulated macro, micro and nano particulates.

As used herein, the term "pre-formed" means that a structure or element is made, constructed, and/or formed into a particular shape or configuration prior to use. Accordingly, the shape or configuration of a pre-formed microneedle array is the shape or configuration of that microneedle array prior to insertion of one or more of the microneedles of the microneedle array into the patient.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernable, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

Tip-Loaded Microneedle Arrays

Dissolvable microneedle arrays enable efficient and safe drug and vaccine delivery to the skin and mucosal surfaces. However, inefficient drug delivery can result from the homogenous nature of conventional microneedle array fabrication. Although the drugs or other cargo that is to be delivered to the patient are generally incorporated into the entire microneedle array matrix, in practice only the microneedles enter the skin and therefore, only cargo contained in the volume of the individual needles is deliverable. Accordingly, the vast majority of the drugs or other cargo that is localized in the non-needle components (e.g., the supporting structure of the array) is never delivered to the patient and is generally discarded as waste.

Figure 2:
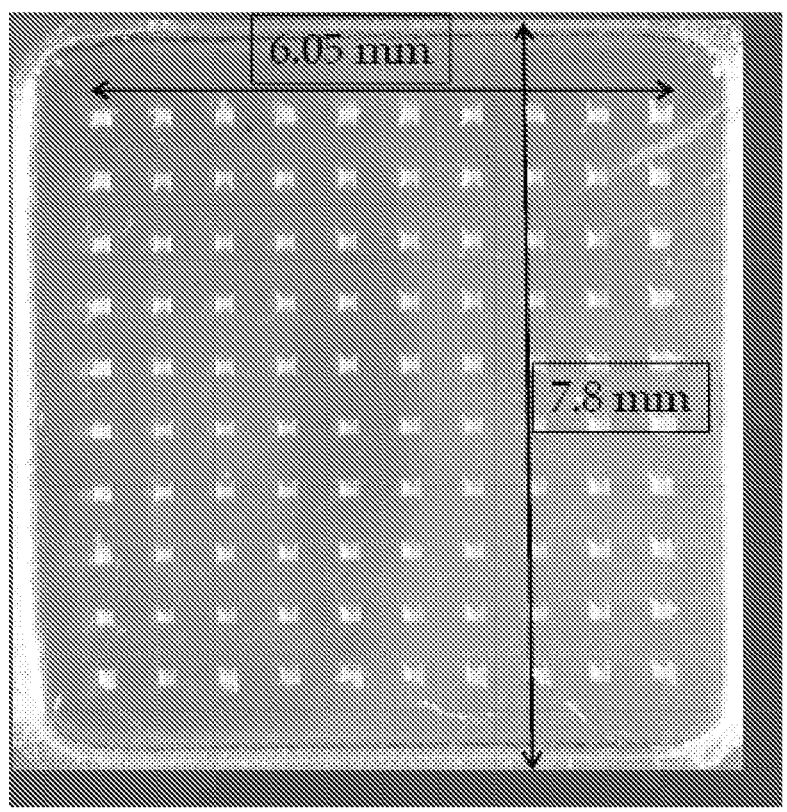
FIG. 2 illustrates an exemplary microneedle array and its dimensions.
Figure 3A:
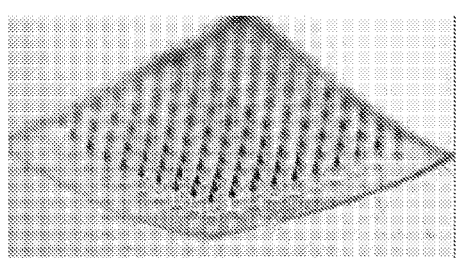
FIGS. 3A and 3B illustrate exemplary microneedles with tip-loaded active components.
Figure 3B:
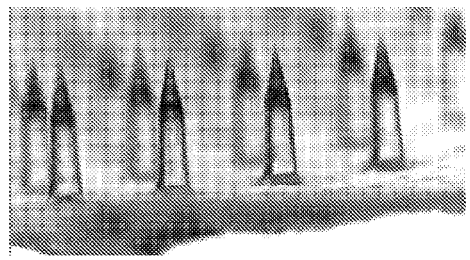
Figure 4A:
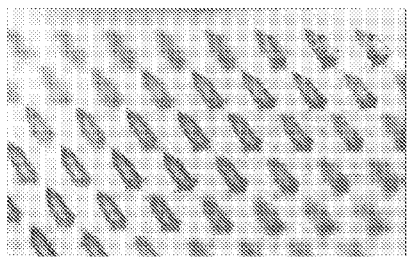
FIGS. 4A and 4B illustrate exemplary microneedles with tip-loaded active components.
Figure 4B:
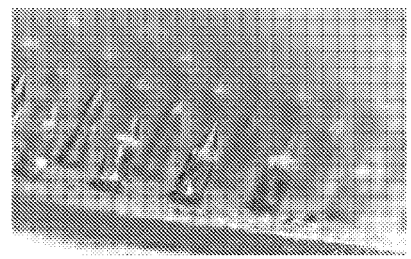

FIGS. 1 and 2 illustrate exemplary dimensions of microneedles and microneedle arrays. Based on the illustrative sizes shown in FIGS. 1 and 2, a microneedle array that comprises an active component homogenously distributed throughout the array exhibits active component waste of greater than 40 percent. For example, if the entire area of the array is 61 mm$^2$ and the microneedle array area is 36 mm$^2$, then the percent utilization of the active component is less than 60 percent. Although the dimensions reflected in FIGS. 1 and 2 illustrate a particular size array and shape of microneedles, it should be understood that similar waste is present in any other size microneedle array in which the active component is homogenously distributed throughout the array, regardless of the size of the array or the shape of the microneedles involved.

The systems and methods described herein provide novel microneedle array fabrication technology that utilizes a fully-dissolvable microneedle array substrate and unique microneedle geometries that enable effective delivery of a broad range of active components, including a broad range of protein and/or small molecule medicines and vaccines.

As described in more detail herein, in some embodiments, this technology can also uniquely enable the simultaneous co-delivery of multiple chemically distinct agents for polyfunctional drug delivery. Examples of the utility of these devices include, for example, (1) simultaneous delivery of multiple antigens and adjuvants to generate a polyvalent immune response relevant to infectious disease prevention and cancer therapy, (2) co-delivery of chemotherapeutic agents, immune stimulators, adjuvants, and antigens to enable simultaneous adjunct tumor therapies, and (3) localized skin delivery of multiple therapeutic agents without systemic exposure for the treatment of a wide variety of skin diseases.

In some embodiments, the systems and method disclosed herein relate to a novel fabrication technology that enables various active components to be incorporated into the needle tips. Thus, by localizing the active components in this manner, the remainder of the microneedle array volume can be prepared using less expensive matrix material that is non-active and generally regarded as safe. The net result is greatly improved efficiency of drug delivery based on (1) reduced waste of non-deliverable active components incorporated into the non-needle portions of the microneedle array, and (2) higher drug concentration in the skin penetrating needle tips. This technological advance results in dramatically improved economic feasibility proportional to the cost of drug cargo, and increased effective cargo delivery capacity per needle of these novel microneedle arrays.

FIGS. 3A, 3B, 4A, and 4B illustrate various embodiments of microneedle arrays wherein the active component is concentrated in the microneedle tips of the respective arrays. Thus, in contrast to conventional microneedle arrays, the active component is not present at even concentration throughout the microneedle array since there is little or no active component present in the supporting base structure. In addition, in some embodiments (as shown, for example, in FIGS. 3A, 3B, 4A, and 4B), not only is there little or no active component in the supporting structures, the location of the active component is concentrated in the upper half of the individual microneedles in the array.

FIGS. 5A and 5B illustrate exemplary images of microneedles of a microneedle array that contains active component concentrated in the upper half of the individual microneedles. The active component is illustrated as fluorescent particles that are concentrated in the tip of the microneedle, with the tip being defined by an area of the microneedle that extends from a base portion in a narrowing and/or tapered manner. The base portion, in turn, extends from the supporting structure of the array.

FIGS. 6A and 6B illustrate additional exemplary images of microneedles of microneedle arrays that contain active components concentrated in the upper half of the individual microneedles. In FIG. 6A, the active component, which is concentrated in the tip of the microneedles, is BSA-FITC. In FIG. 6B, the active component, which is also concentrated in the tip of the microneedles, is OVA-FITC.

As noted above, in some embodiments, individual microneedles can comprise active components only in the upper half of the microneedle. In other embodiments, individual microneedles can comprise active components only in the tips or in a narrowing portion near the tip of the microneedle. In still other embodiments, individual needles can comprise active components throughout the entire microneedle portion that extends from the supporting structure.

The following embodiments describe various exemplary methods for fabricating microneedle arrays with one or more active component concentrated in the upper halves and/or tips of microneedles in respective microneedle arrays.

Microneedle Arrays Fabricated by Sequential Micro-Molding and Spin-Drying Methods The following steps describe an exemplary method of fabricating microneedle arrays using sequential micro-molding and spin-drying. Active components/cargo can be prepared at a desired useful concentration in a compatible solvent. As described herein, the solvents of the active component(s) can be cargo specific and can comprise a broad range of liquids, including for example, water, organic polar, and/or apolar liquids. Examples of active components are discussed in more detail below and various information about those active components, including tested and maximum loading capacity of various microneedle arrays are also discussed in more detail below.

If desired, multiple loading cycles can be performed to achieve higher active cargo loads as necessary for specific applications. In addition, multiple active cargos can be loaded in a single loading cycle as a complex solution, or as single solutions in multiple cycles (e.g., repeating the loading cycle described below) as per specific cargo-compatibility requirements of individual cargos. Also, particulate cargos (including those with nano- and micro-sized geometries) can be prepared as suspensions at the desired particle number/volume density.

Figure 9:
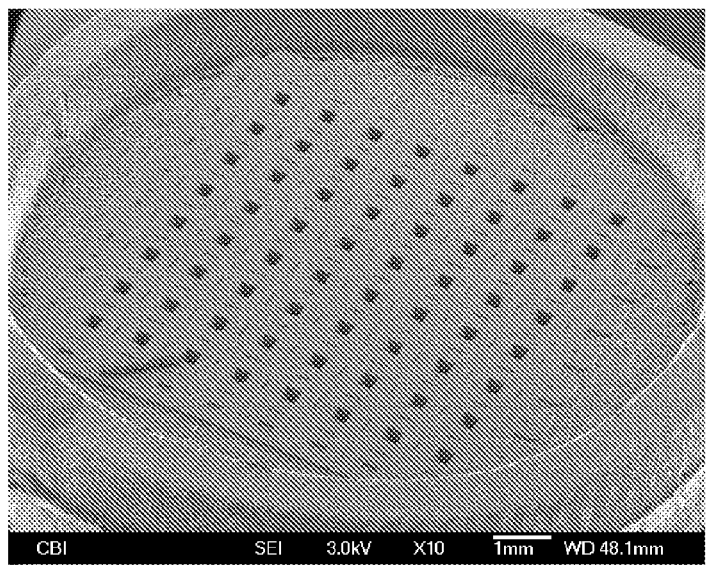
FIG. 9 is an SEM image of a pyramidal production mold.

Example 1 a) As described in more detail below in the micromilling embodiments, an active cargo's working stock solution/suspension can be applied to the surface of microneedle array production molds at, for example, about 40 µl per cm$^2$ surface area.

b) The microneedle array production molds with active cargo(s) can be centrifuged at 4500 rpm for 10 minutes to fill the microneedle array production molds needles with the working cargo stock.

c) The excess cargo solution/suspension can be removed and the surface of the microneedle array production molds, washed with 100 µl phosphate buffer saline (PBS) per cm$^2$ mold-surface area, or with the solvent used for the preparation of the active cargo's working stock.

d) The microneedle array production molds containing the active cargo stock solution/suspension in the needle's cavity can be spin-dried at 3500 rpm for 30 minutes at the required temperature with continues purging gas flow through the centrifuge at 0-50 L/min to facilitate concentration of the drying active cargo(s) in the needle-tips. The purging gas can be introduced into the centrifuge chamber through tubular inlets. Moisture content can be reduced using a dehumidifier tempered to the required temperature with recirculation into the centrifuge chamber. The purging gas can be air, nitrogen, carbon dioxide or another inert or active gas as required for specific cargo(s). The flow rate is measured by flow-meters and controlled by a circulating pump device.

e) 100 µl 20% CMC90 hydrogel in H2O can be added to the surface microneedle array production molds' per cm² microneedle array production molds-area to load the structural component of the microneedle array device.

f) The microneedle array production molds can be centrifuged at 4500 rpm for 10 min at the required temperature without purging gas exchange in the centrifuge chamber to fill up the microneedle array production molds needle cavities with the CMC90 hydrogel. This can be followed by a 30 min incubation period to enable rehydration of the active cargo(s) previously deposited in the microneedle array tips.

g) The microneedle array production molds can centrifuged at 3500 rpm for 3 hours or longer at the required temperature with 0-50 L/min constant purging gas flow through the centrifuge chamber to spin-dry the MNA devices to less than 5% moisture content.

h) The dried microneedle array devices can then be separated from the microneedle array production molds for storage under the desired conditions. In some embodiments, CMC90 based devices can be storable between about 50° C. to −86° C.

Examples of fabricated tip-loaded active cargo carrying microneedle arrays can be seen in FIGS. 3A-6B.

Micromilled Master Molds and Spin-Molded Microneedle Arrays

In the following embodiments, micromilling steps are preformed to create microneedle arrays of various specifications. It should be understood, however, that the following embodiments describe certain details of microneedle array fabrication that can be applicable to processes of microneedle array fabrication that do not involve micromilling steps, including the process described above in the previous example.

In the following embodiments, apparatuses and methods are described for fabricating dissolvable microneedle arrays using master molds formed by micromilling techniques. For example, microneedle arrays can be fabricated based on a mastermold (positive) to production mold (negative) to array (positive) methodology. Micromilling technology can be used to generate various micro-scale geometries on virtually any type of material, including metal, polymer, and ceramic parts. Micromilled mastermolds of various shapes and configurations can be effectively used to generate multiple identical female production molds. The female production molds can then be used to microcast various microneedle arrays.

FIG. 7 illustrates an example of a precision-micromilling system that can be used for fabricating a microneedle mastermold. Mechanical micromilling uses micro-scale (for example, as small as 10 μm) milling tools within precision computer controlled miniature machine-tool platforms. The system can include a microscope to view the surface of the workpiece that is being cut by the micro-tool. The micro-tool can be rotated at ultra-high speeds (200,000 rpm) to cut the workpiece to create the desired shapes. As noted above, the micromilling process can be used to create complex geometric features with many kinds of material. Various types of tooling can be used in the micromilling process, including, for example, carbide micro-tools. In a preferred embodiment, however, diamond tools can be used to fabricate the microneedle arrays on the master mold. Diamond tooling can be preferable over other types of tooling because it is harder than conventional materials, such as carbide, and can provide cleaner cuts on the surface of the workpiece.

Mastermolds can be micromilled from various materials, including, for example, Cirlex® (DuPont, Kapton® polyimide), which is the mastermold material described in the exemplary embodiment. Mastermolds can be used to fabricate flexible production molds from a suitable material, such as SYLGARD® 184 (Dow Corning), which is the production material described in the exemplary embodiment below. The mastermold is desirably formed of a material that is capable of being reused so that a single mastermold can be repeatedly used to fabricate a large number of production molds. Similarly each production mold is desirably able to fabricate multiple microneedle arrays.

Mastermolds can be created relatively quickly using micromilling technology. For example, a mastermold that comprises a 10 mm×10 mm array with 100 microneedles can take less than a couple of hours and, in some embodiments, less than about 30 minutes to micromill. Thus, a short ramp-up time enables rapid fabrication of different geometries, which permits the rapid development of microneedle arrays and also facilitates the experimentation and study of various microneedle parameters.

The mastermold material preferably is able to be cleanly separated from the production mold material and preferably is able to withstand any heighted curing temperatures that may be necessary to cure the production mold material. For example, in an illustrated embodiment, the silicone-based compound SYLGARD® 184 (Dow Corning) is the production mold material and that material generally requires a curing temperature of about 80-90 degrees Celsius.

Mastermolds can be created in various sizes. For example, in an exemplary embodiment, a mastermold was created on 1.8 mm thick Cirlex® (DuPont, Kapton® polyimide) and 5.0 mm thick acrylic sheets. Each sheet can be flattened first by micromilling tools, and the location where the microneedles are to be created can be raised from the rest of the surface. Micro-tools can be used in conjunction with a numerically controlled micromilling machine (FIG. 1) to create the microneedle features (e.g., as defined by the mastermold). In that manner, the micromilling process can provide full control of the dimensions, sharpness, and spatial distribution of the microneedles.

FIG. 8 is an image from a scanning electron microscope (SEM) showing the structure of a micromilled mastermold with a plurality of pyramidal needles. As shown in FIG. 8, a circular groove can be formed around the microneedle array of the mastermold to produce an annular (for example, circular) wall section in the production mold. The circular wall section of the production mold can facilitate the spin-casting processes discussed below. Although the wall sections illustrated in FIG. 9 and the respective mastermold structure shown in FIG. 8 is circular, it should be understood that wall sections or containment means of other geometries can be provided. For example, depending on what shape is desired for the microneedle array device, the containment means can be formed in a variety of shapes including, for example, square, rectangular, trapezoidal, polygonal, or various irregular shapes.

As discussed above, the production molds can be made from SYLGARD® 184 (Dow Corning), which is a two component clear curable silicone elastomer that can be mixed at a 10:1 SYLGARD® to curing agent ratio. The mixture can be degassed for about 10 minutes and poured over the mastermold to form an approximately 8 mm layer, subsequently degassed again for about 30 minutes and cured at 85° C. for 45 minutes. After cooling down to room temperature, the mastermold can be separated from the cured silicone, and the silicone production mold trimmed to the edge of the circular wall section that surrounds the array (FIG. 9.). From a single mastermold, a large number of production molds (e.g., 100 or more) can be produced with very little, if any, apparent deterioration of the Cirlex® or acrylic mastermolds.

Figure 10:
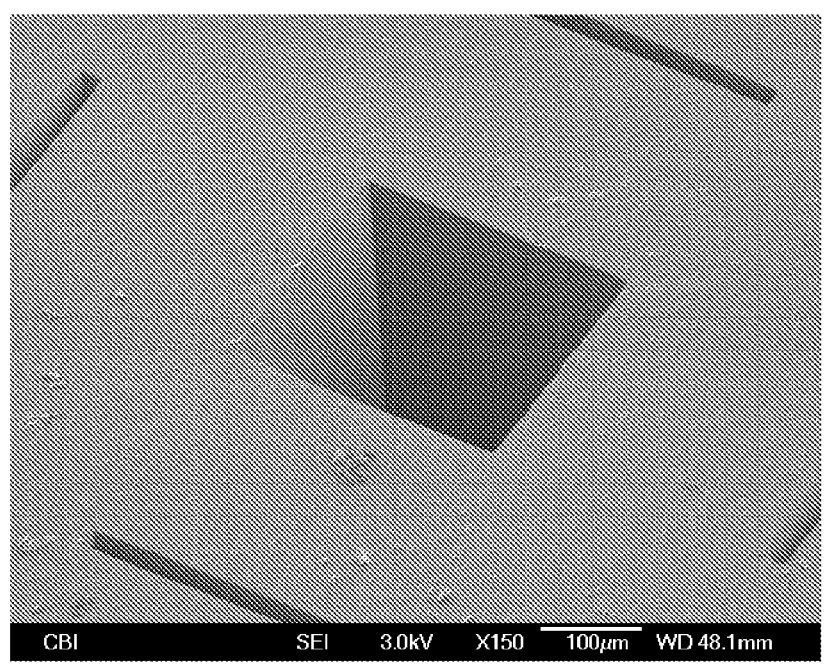
FIG. 10 is an SEM image of an enlarged segment of the production mold, illustrating a pyramidal needle molding well in the center of the image.

FIG. 9 is an SEM image of a pyramidal production mold created as described above. FIG. 10 illustrates an enlarged segment of the production mold with a pyramidal needle molding well in the center of the image. The molding well is configured to receive a base material (and any components added to the base material) to form microneedles with an external shape defined by the molding well.

To construct the microneedle arrays, a base material can be used to form portions of each microneedle that have bioactive components and portions that do not. As discussed above, each microneedle can comprise bioactive components only in the microneedles, or in some embodiments, only in the upper half of the microneedles, or in other embodiments, only in a portion of the microneedle that tapers near the tip. Thus, to control the delivery of the bioactive component(s) and to control the cost of the microneedle arrays, each microneedle preferably has a portion with a bioactive component and a portion without a bioactive component. In the embodiments described herein, the portion without the bioactive component includes the supporting structure of the microneedle array and, in some embodiments, a base portion (e.g., a lower half) of each microneedle in the array.

Various materials can be used as the base material for the microneedle arrays. The structural substrates of biodegradable solid microneedles most commonly include poly(lactic-co-glycolic acid) (PLGA) or carboxymethylcellulose (CMC) based formulations; however, other bases can be used.

CMC is generally preferable to PLGA as the base material of the microneedle arrays described herein. The PLGA based devices can limit drug delivery and vaccine applications due to the relatively high temperature (e.g., 135 degrees Celsius or higher) and vacuum required for fabrication. In contrast, a CMC-based matrix can be formed at room temperature in a simple spin-casting and drying process, making CMC-microneedle arrays more desirable for incorporation of sensitive biologics, peptides, proteins, nucleic acids, and other various bioactive components.

CMC-hydrogel can be prepared from low viscosity sodium salt of CMC with or without active components (as described below) in sterile dH$_2$O. In the exemplary embodiment, CMC can be mixed with sterile distilled water (dH$_2$O) and with the active components to achieve about 25 wt % CMC concentration. The resulting mixture can be stirred to homogeneity and equilibrated at about 4 degrees Celsius for 24 hours. During this period, the CMC and any other components can be hydrated and a hydrogel can be formed. The hydrogel can be degassed in a vacuum for about an hour and centrifuged at about 20,000 g for an hour to remove residual micro-sized air bubbles that might interfere with a spincasting/drying process of the CMC-microneedle arrays. The dry matter content of the hydrogel can be tested by drying a fraction (10 g) of it at 85 degrees Celsius for about 72 hours. The ready-to-use CMC-hydrogel is desirably stored at about 4 degrees Celsius until use.

Active components can be incorporated in a hydrogel of CMC at a relatively high (20-30%) CMC-dry biologics weight ratio before the spin-casting process. Arrays can be spin-cast at room temperature, making the process compatible with the functional stability of a structurally broad range of bioactive components. Since the master and production molds can be reusable for a large number of fabrication cycles, the fabrication costs can be greatly reduced. The resulting dehydrated CMC-microneedle arrays are generally stable at room temperature or slightly lower temperatures (such as about 4 degrees Celsius), and preserve the activity of the incorporated biologics, facilitating easy, low cost storage and distribution.

In an exemplary embodiment, the surface of the production molds can be covered with about 50 µl (for molds with 11 mm diameter) of CMC-hydrogel and spin-casted by centrifugation at 2,500 g for about 5 minutes. After the initial CMC-hydrogel layer, another 50 µl CMC-hydrogel can be layered over the mold and centrifuged for about 4 hours at 2,500 g. At the end of a drying process, the CMC-microneedle arrays can be separated from the molds, trimmed off from excess material at the edges, collected and stored at about 4 degrees Celsuis. The production molds can be cleaned and reused for further casting of microneedle arrays.

In some embodiments, CMC-solids can be formed with layers that do not contain active components and layers that contain active components. FIGS. 11A-D illustrate CMC-solids with different shapes (FIGS. 11A and 11B) and embedded active cargos on an upper layer which becomes, after micromilling, the portions of the microneedle with the active components. FIG. 11C illustrates micron sized fluorescent particles layered on a surface of a non-active component containing layer and FIG. 11D illustrates toluidine blue examples layered on a surface of a non-active component containing layer.

FIGS. 12A and 12B also illustrate CMC-solids with different shapes, with FIG. 12B showing a square shape and FIG. 12B showing a rectangular shape. Both CMC solids can be milled to dimensions for further processing as described herein. It should be understood that the geometries and the active cargo shown herein are not intended to be limited to the exemplary embodiments.

Example 2

CMC-solids can be prepared with defined geometry and active cargo contents in one or more layers of the prepared structure. Examples of active cargos integrated into CMC-solids are described more detail herein. Upon construction of the CMC-solids with embedded active cargo contained in at least one layer of the CMC-solid, the CMC solids can be milled to project-specific dimensions and micro-milled to fabricate microneedle devices as described herein.

Example 3

Figure 13:
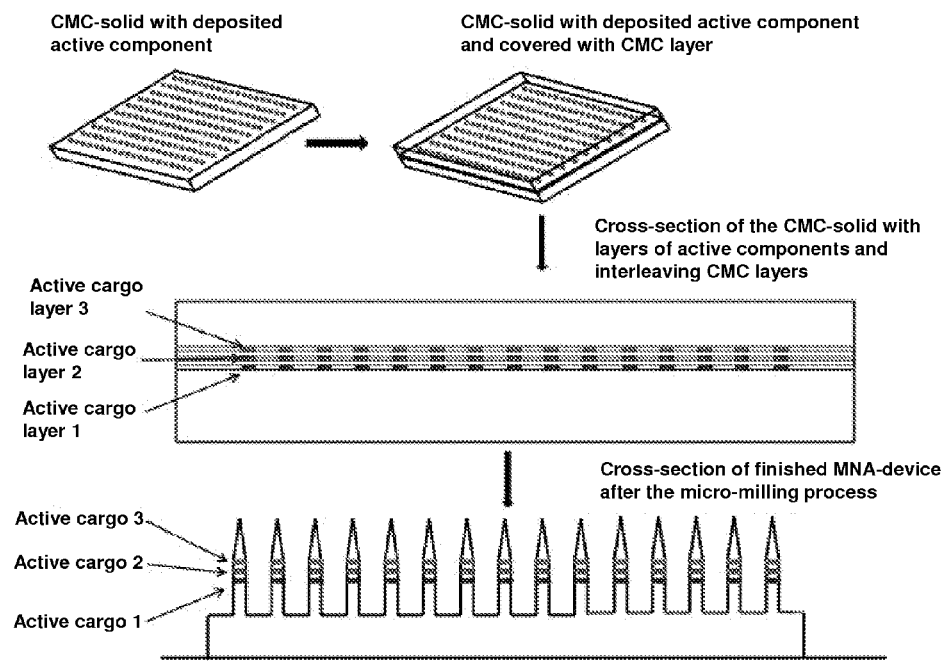
FIG. 13 is a schematic illustration of exemplary vertical multi-layered deposition structures and methods of fabricating the same.

In another embodiment, one or more layers of active cargo can be embedded on CMC-solids for direct micromilling of the microneedle array. FIG. 13 illustrates a sample representation of vertical multi-layered deposition and CMC embedding of active cargos on CMC-solids for direct micromilling of MNA devices.

In one exemplary method, microneedle arrays can be fabricated by preparing CMC-solids with a defined geometries and without any active cargo contained therein. Then, blank CMC-solids can be milled to a desired dimension.

As shown in FIG. 13, active cargo(s) can be deposited onto the CMC-solid in project specific geometric patterns for inclusion of the active cargo(s) specifically in the tips of micro-milled MNA devices.

The methods active cargo deposition onto the CMC-solid blank can include, for example:

1) Direct printing with micro-nozzle aided droplet deposition.

2) Transfer from preprinted matrices.

3) Droplet-deposition with computer controlled robotic systems.

Figure 14:
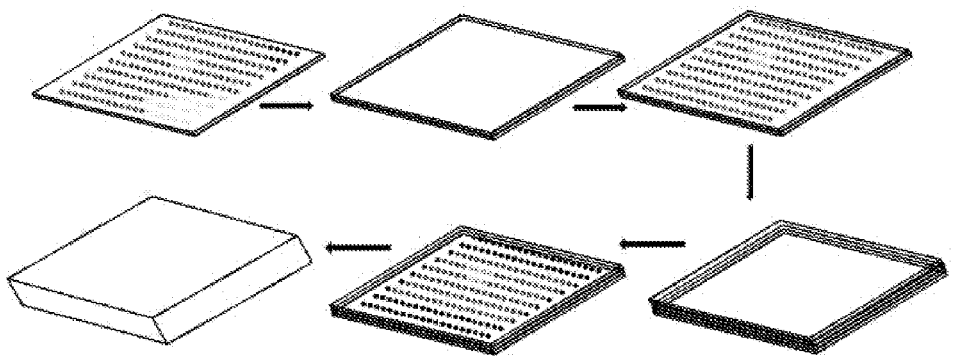
FIG. 14 is a schematic illustration of exemplary microneedle arrays fabricated using layering and spatial distribution techniques of embedded active components.

FIG. 14 illustrates layering and spatial distribution of embedded active cargos in a CMC-solid block. After the first layer is deposited (A) it can be covered with a CMC layer (B) that provides the surface for the subsequent deposition of the active cargo (C). The process can be repeated until all desired layers are deposited and encased in a solid CMC-block suitable for the micro-milling process (D-F).

FIG. 15 illustrates a schematic view of a cross-section of a CMC-block encasing the deposits of the active cargo in a spatially controlled manner (A). The method allows 3-dimensional control and placement of the active components after micro-milling in the MNA-device (B). In panel (B) of FIG. 15, the placement of the active cargos are shown in the stems of the active cargo; however through the control of the milling process the placement can be controlled vertically from the tip to the base of the microneedles. Colors represent different active components or different amount/concentration of the same material.

Thus, a method of vertically layered deposition of active cargos in microneedles is provided by depositing one or more active cargos sequentially on the surface of the CMC-solids in contact with each other or separated by layers of CMC. In some embodiments, horizontal pattern deposition of the active cargos can result in spatial separation of the cargos. By combining vertical and horizontal patterning of active cargo deposition, 3 dimensional delivery and distribution of each of the defined active components can be achieved, further reducing waste of active components during fabrication of microneedle arrays.

Microneedle Integrated Adenovectors

The following embodiments are directed to dissolvable microneedle arrays, such as those described herein, that incorporate infectious viral vectors into the dissolvable matrix of microneedle arrays. Using this technology, for the first time, living viral vectors can be incorporated into microneedle arrays. As described herein, the incorporation of viral vectors within the disclosed microneedle arrays stabilizes the viral vectors so that they maintain their infectivity after incorporation and after prolonged periods of storage. The application of microneedle array incorporated adenovectors (MIAs) to the skin results in transfection of skin cells. In a vaccine setting, we have demonstrated that skin application of MIAs encoding an HIV antigen results in potent HIV specific immune responses. These results are described in detail in the examples below.

Example 4

The microneedle integrated adenovectors preparation method described herein preserves the viability of the adenoviral particles during the preparation and in dry storage. These steps were specifically designed based on the physical and chemical properties of CMC microneedle arrays. Viral viability in CMC microneedle arrays was achieved by Inclusion of low viscosity carboxymethyl cellulose (CMC90) at 2.5% final concentration (step 2.) and by
Timed and temperature controlled spin-drying concentration of the adenoviral particles in the tips of the microneedle array devices (step 6.).
Controlled partial rehydration of the needle-tip loaded adenoviral particles (step 8.)

Preparation of Tip-Loaded Microneedle Integrated Adenovectors (MIAs):

1) Resuspend adenoviral particles at $2\times10^9$ particles/ml density in Trehalose-storage buffer (5% trehalose Sigma-Aldrich USA, 20 mM Tris pH7.8, 75 mM NaCl, 2 mM $MgCl_2$, 0.025% Tween 80)

2) Mix resuspended viral stock with equal volume of 5% CMC90 prepared in Trehasole-storage buffer, resulting in a $1\times10^9$ particles/ml density adenoviral working stock.

3) Add adenoviral working stock suspension to the surface of microneedle array production molds (as described in detail in other embodiments herein) at 40 µl per $cm^2$ surface area.

4) The molds are centrifuged at 4500 rpm for 10 minutes at 22° C. to fill the needle tips with adenoviral working stock.

5) The excess viral stock is removed and the surface of the molds washed with 100 µl (phosphate buffer saline (PBS) solution per $cm^2$ mold-surface area.

6) The microneedle array-molds containing the adenoviral stock solution only in the needle's cavity are partially spin-dried at 3500 rpm for 10 minutes at 22° C.

7) 100 µl 20% structural, non-cargo containing CMC90 hydrogel in $H_2O$ added to the surface microneedle array-molds' per $cm^2$ mold-area to form the structure of the MIA device.

8) Centrifuge at 4500 rpm for 10 min at 22° C. to fill up the needle cavities with 20% CMC90 and allow 30 min incubation for the rehydration of the adenoviral particles dried in the tips (step 3-6, above).

9) By centrifugation spin-dry the MIA devices to less than 5% moisture content at 3500 rpm for 3 hours at 22° C. with 10 L/min constant air flow through the centrifuge chamber.

10) De-mold the dried MIA devices for storage at 4° C. or −80° C.

Example 5

We have evaluated the potency and stability MNA incorporated recombinant adenoviral particles. Ad5.EGFP was incorporated into CMC hydrogel MNAs to fabricate a final product that contained $10^{10}$ virus particles/MNA. Control blank MNAs were prepared identically but without the virus. Batches of Ad5.EGFP and control MNAs were stored at RT, 4° C. and at −86° C. and viral stability was evaluated in infectious assays. Specific transduction activity of the MNA incorporated Ad5.EGFP virus was assessed in vitro using 293T cells. Cells were plated at $2\times10^6$/well in six well plates and transduced in duplicate with diluted virus suspension, suspension+empty MNA (control), or Ad5.EGFP MNAs stored at RT, 4° C. and −86° C. for the indicated time periods. As a negative control untransduced wells were included. Initially cell populations were analyzed after 24 h by flow cytometry for GFP expression (representative histogram is shown in FIG. 35.).

Figure 35:
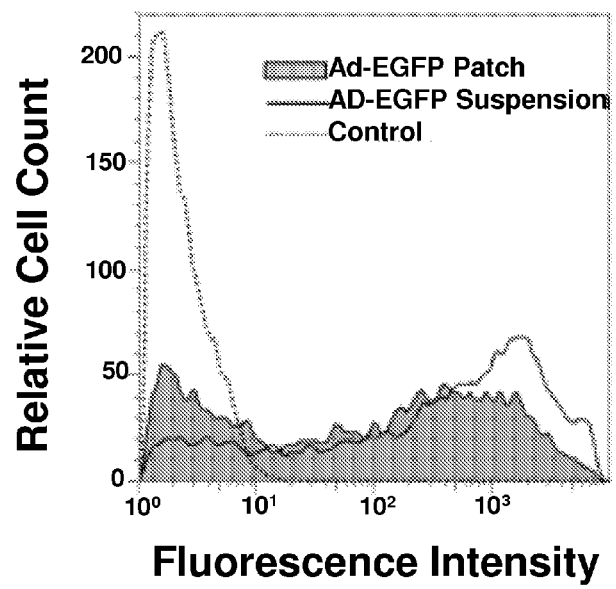
FIG. 35 is a flow cytometry analysis of GFP expressing target 293T cells.
Figure 36:
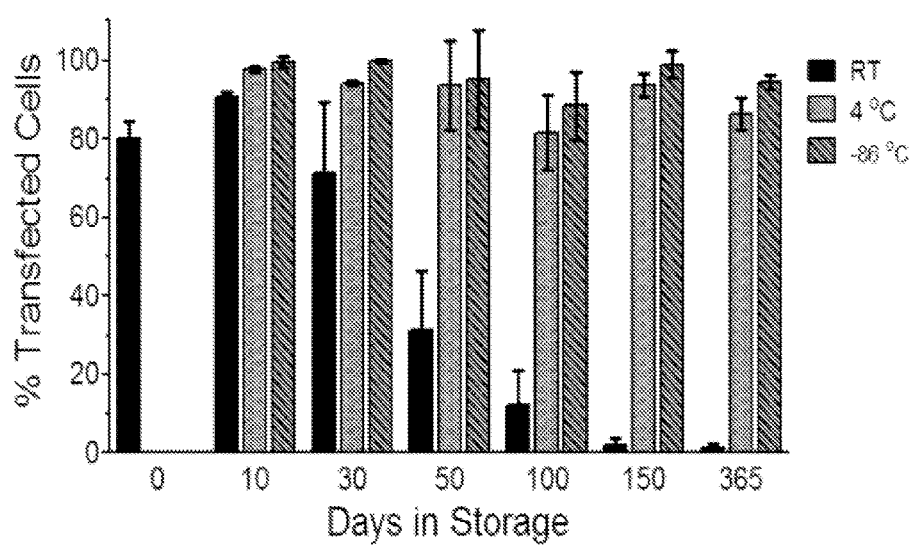
FIG. 36 illustrates the stability of microneedle embedded viruses after a number of days in storage.

As shown in FIG. 35, the incorporation of Ad5.EGFP into MNAs does not reduce transduction efficiency. Flow cytometry analysis of GFP expressing target 293T cells 24 h after transduction with identical titers of Ad5.EGFP either in suspension or incorporated into CMC-patches vs. untransfected control cells. FIG. 36 shows the stability of MNA embedded Ad5.EGFP virus. GFP gene expression was assayed by flow cytometry as in FIG. 37 and normalized to the infection efficiency of −86° C. preserved Ad5.EGFP suspension.

It has been found that the infection efficiency using MNA Ad5.EGFP virus was 87.92±4.5%, which is similar to that observed for traditional −86° C. preserved Ad5.EGFP suspension (FIGS. 35 and 36), suggesting that the manufacturing process does not adversely affect the transduction efficiency of Ad-EGFP viral particles. To asses infectivity over time, the transfection efficiency of freshly prepared −86° C. preserved Ad5.EGFP suspensions was compared to that of MNA incorporated Ad5.EGFP stored for prolonged periods of time at either RT, 4 C, or −86 C. Infectivity (normalized to Ad5.EGFP suspension+empty CMC-patch) is reported for storage periods of up to 365 days (FIG. 36). These results suggest that the infectiousness of MNA Ad5.EGFP is remarkably stable with storage at either 4 C or −86 C, and somewhat stable at RT for up to 30 days.

Figure 37:
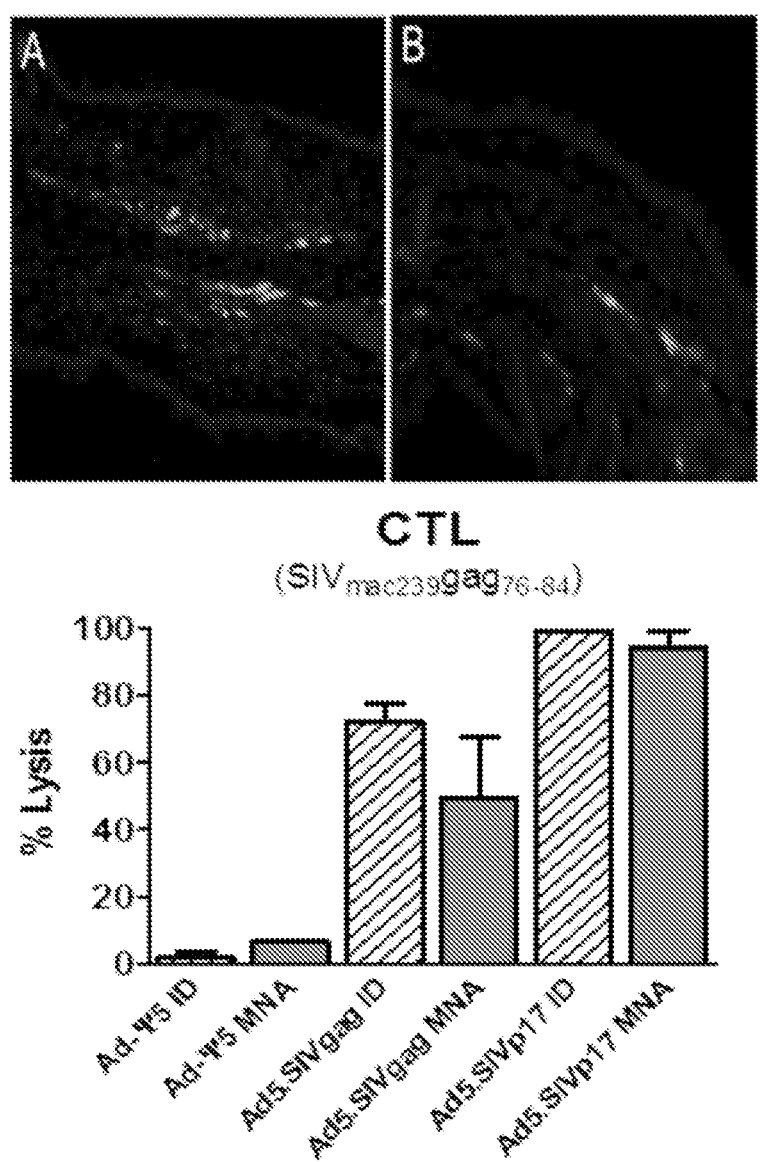
FIG. 37 illustrates the expression and immunogenicity of microneedle array delivered adenovectors.

These results demonstrate that microneedle array delivered Ad transgenes are expressed in the skin and induce potent cellular immune responses. To specifically evaluate gene expression in vivo, we determined GFP expression in skin following either traditional intradermal injection (I.D.) or microneedle array-mediated intracutaneous delivery. We delivered 108 Ad5.GFP viral particles by ID injection or topically via a single microneedle array application (FIG. 37). Skin was harvested 48 h later, cryosectioned, counterstained using blue fluorescent DAPI to identify cell nuclei, and then imaged by fluorescent microscopy. Significant cellular GFP expression was observed following both I.D. and microneedle array delivery. To evaluate immunogenicity, we evaluated antigen-specific lytic activity in vivo following a single I.D. or microneedle array immunization without boosting. For this purpose we immunized groups of mice with E1/E3-deleted Ad5-based vectors that encode codon-optimized SIVmac239 gag full-length or SIVmac239 gag p17 antigens (Ad5.SIV gag, Ad5.SIV gag p17). Empty vector was used as a control (Ad5). We observed potent and similar levels of in vivo lytic activity specific for the dominant SIVgag p17-derived peptide KSLYNTVCV (SIVmac239 gag 76-84) following either I.D. or microneedle array immunization with either Ad5.SIV gag or Ad5.SIV gag p17 (FIG. 37, CTL).

The microneedle array technology disclosed herein can also facilitate clinical gene therapy. It addresses, for example, at least two major limitations of conventional approaches. First, it enables stabilization and storage of recombinant viral vectors for prolonged periods of time. By rendering live virus vectors resistant to high and low temperatures with proven seroequivalence to frozen liquid formulations, microneedle array stabilization will relieve pressures related to the 'cold chain.' Further, integration in microneedle arrays enables precise, consistent and reproducible dosing of viral vectors not achievable by conventional methods. Finally, the viral vector is repackaged in the only necessary delivery device, the biocompatible and completely disposable microneedle array that directs delivery precisely to the superficial layers of the skin.

Such a gene delivery platform is useful in providing patient-friendly, clinical gene therapy. Since these microneedle arrays have been engineered to not penetrate to the depth of vascular or neural structures, gene delivery to human skin will be both painless and bloodless. In addition, the fabrication process is flexible, enabling simple and rapid low cost production with efficient scale-up potential. Also, as a final product, the MIA device it is stable at room temperature and is inexpensive to transport and store. In combination, these structural and manufacturing advantages can enable broad and rapid clinical deployment, making this gene delivery technology readily applicable to the prevention and/or treatment of a broad range of human diseases. Moreover, this approach can be extended to other vector-based vaccine platforms that are currently restricted by the same limitations (e.g., vaccinia virus, AAV etc.). For at least these reasons, the disclosed microneedle arrays and methods of using the same significantly advance the recombinant gene therapy field.

Microneedle Arrays—Exemplary Active Components

Various active components are described in detail below. For convenience, the following examples are based on an microneedle array which is 6.3×6.3 mm. This size, and hence cargo delivery can be varied by increasing or decreasing 2-100 fold.

General considerations for the maximum active cargo quantities include, for example, total needle volume in the array and solubility of the active component(s) in the solvent (generally expected to be <50%).

| Tip Loaded Components: | Amount Tip Loaded into MNA device µg/device (unless indicated differently) | Max. predicted loading capacity |
|---|---|---|
| Live viruses[1] | | |
| Ad5.GFP (adeno viral GFP expression vector) | $5 \times 10^8$ particles/MNA | $2\text{-}5 \times 10^9$ particles/MNA |
| Ad-SIVgag (adeno viral gag expression vector) | $5 \times 10^8$ particles/MNA | $2\text{-}5 \times 10^9$ particles/MNA |
| Ad-SIVp17 (adeno viral gag-p17 expression vector) | $5 \times 10^8$ particles/MNA | $2\text{-}5 \times 10^9$ particles/MNA |
| Ψ5 (non-recombinant Ad vector) | $5 \times 10^8$ particles/MNA | $2\text{-}5 \times 10^9$ particles/MNA |
| Lenti-GFP[2] (Lenti viral GFP expression vector) | $5 \times 10^6$ particles/MNA | $2\text{-}5 \times 10^7$ particles/MNA |

Vaccinia virus (immunization)
Recombinant vaccinia virus (gene therapy, genetic engineering)
Seasonal influenza
MMR (Measles, Mumps, Rubella)

| Proteins/Peptides | | |
|---|---|---|
| BSA (FITC labeled) | 240 | 400 |
| OVA (FITC labeled) | 100 | 400 |
| OVA (no label) | 240 | 400 |
| Flu (split vaccine) | 0.22 | (2-5) |
| Epitope Peptides[3] | | |
| TRP-2 | 50 | 200 |
| EphA2 (a) | 50 | 400 |
| EphA2 (b) | 50 | 400 |
| DLK-1 | 50 | 200 |
| Multiple epitopes in one MNA | 200 | 400-600 |
| Substance-P (NK-1R ligand) | 15 | |
| Nucleic acids | | |
| CpG 1668 | 120 | 250 |
| CpG 2006 | 120 | 250 |
| Poly(I:C) | 250 | 250 |
| Plasmid vectors (High mol. weight DNA) | 100 | 200 |
| Peptides/Nucleic acid combos | | |
| OVA/CpG | 250/120 | |
| OVA/CpG/poly(I:C) | 250/120/250 | |
| Epitope peptides/poly(I:C) | 200/250 | |
| Organics | | |
| Doxorubicin | 100 | |
| R848 (TLR7/8 ligand) | 6 | |

-continued

| | | |
|---|---|---|
| L733 (NK-1 antagonist) | 2 | |
| DNCB (irritant) | 100 | |
| Particulates | | |
| Micro-particles (1 µ diameter microsphares) | $1 \times 10^6$ particles/MNA | $2\text{-}5 \times 10^7$ particles/MNA |

Nano Scale Particles
PLG/PLA Based

| Other Biologic | |
|---|---|
| tumor lysate/CpG | 250/120 |
| tumor lysate/CpG/poly(I:C) | 250/120/250 |
| tumor lysates/poly(I:C) | 200/250 |

Tip-loading of live adenoviruses generally includes the following modifications:

a) The presence of 5% trehalose and 2.5% CMC90 in the tip-loading hydrogel suspension.

b) The temperature of the process is maintained at 22° C. In addition, Lenti viral vectors generally require 4° C. processing and vapor trap based humidity controls. Also, short epitope peptides generally are solubilized in DMSO, with the evaporation time of the solvent during tip-loading is 4 hours.

Microneedle Structures and Shapes

For each of the embodiments below, it should be understood that one or more layers of active components can be provided in the microneedles of the microneedle arrays as described above. Thus, for example, in some embodiments, active components are only provided in the area of the microneedle—not in the structural support of the array, such as shown in FIG. 15. Moreover, in other embodiments, the active components are concentrated in the upper half of the microneedles, such as in the tips of the microneedles as shown in FIGS. 3A-4B.

Figures 16A, 16B:
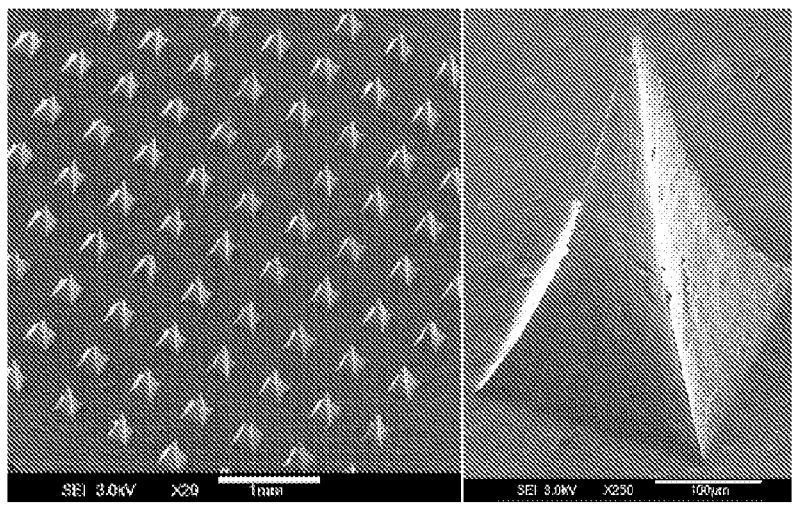
FIG. 16A is an SEM image of a plurality of pyramidal-type molded microneedles.
FIG. 16B is an SEM image of a single pyramidal-type molded microneedle.

FIGS. 16A and 16B are SEM images of a CMC-microneedle array formed with a plurality of pyramidal projections (i.e., microneedles). The average tip diameter of the pyramidal needles shown in FIG. 16A is about 5-10 µm. As shown in FIG. 16B, the sides of the pyramidal needles can be formed with curved and/or arcuate faces that can facilitate insertion in skin.

Figure 17:
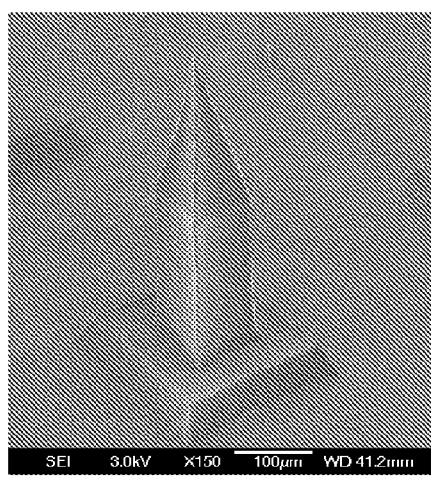
FIG. 17 is an SEM image of a pillar type molded microneedle.

FIG. 17 is another SEM image of a single needle of a microneedle array. The microneedle shown in FIG. 17 is a base-extended pillar type molded CMC-microneedle. The base-extended pillar type microneedle comprises a base portion, which is generally polygonal (for example, rectangular) in cross section, and a projecting portion that extends from the base portion. The projecting portion has a lower portion that is substantially rectangular and tip portion that generally tapers to a point. The tip portion is generally pyramidal in shape, and the exposed faces of the pyramid can be either flat or arcuate. The projecting portion can be half or more the entire length of the needle.

Figure 18:
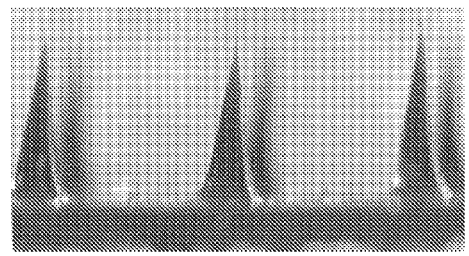
FIG. 18 is a micrograph of pyramidal type molded microneedles.
Figure 19:
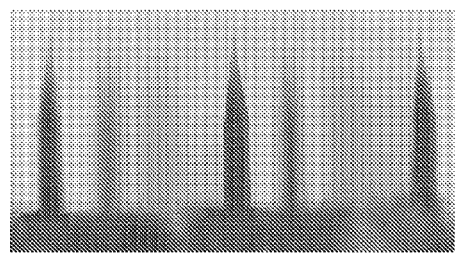
FIG. 19 is a micrograph of pillar type molded microneedles.

FIGS. 18 and 19 illustrate micrographs of pyramidal (FIG. 18) and pillar type (FIG. 19) molded CMC-microneedles. Because the pyramidal needles have a continually increasing cross-sectional profile (dimension) from the needle point to the needle base, as the needle enters the skin, the force required to continue pushing the pyramidal needle into the skin increases. In contrast, pillar type needles have a generally continuous cross-sectional profile (dimension) once the generally rectangular portion of the projection portion is reached. Thus, pillar type needles can be preferable over pyramidal type needles because they can allow for the introduction of the needle into the skin with less force.

Figure 8:
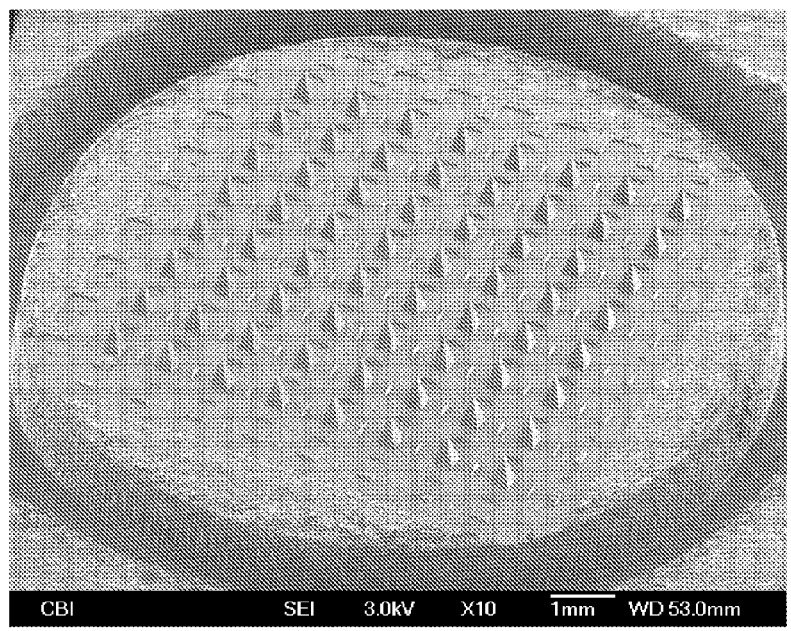
FIG. 8 is an SEM image of a micromilled mastermold with pyramidal needles.
Figure 20:
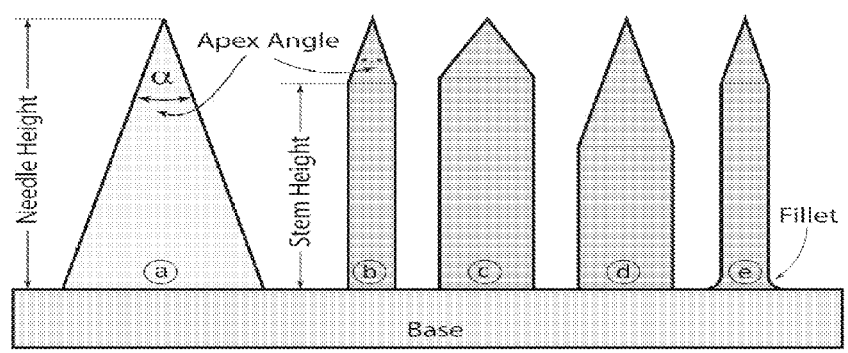
FIG. 20 illustrates various microneedle geometries that can be formed using micromilled mastermolds or by direct micromilling of a block of material.

FIG. 20 illustrates schematic representation of microneedle shapes and structures that are generally suitable for fabrication by spin-casting material into a mastermold formed by micromilling. Since the shapes and structures shown in FIG. 20 do not contain any undercuts, they generally will not interfere with the molding/de-molding process. The structures in FIG. 20 include (a) a generally pyramidal microneedle, (b) a "sharp" pillar type microneedle (without the base member of FIG. 8), (c) a "wide" pillar type microneedle, (d) a "short" pillar type microneedle (having a short pillar section and a longer pointed section), and (e) a "filleted" pillar type microneedle.

While the volume of the pyramidal microneedles can be greater than that of the pillar type microneedles, their increasing cross-sectional profile (dimension) requires an increasing insertion force. Accordingly, the geometry of the pyramidal microneedles can result in reduced insertion depths and a reduced effective delivery volume. On the other hand, the smaller cross-sectional area and larger aspect ratio of the pillar microneedles may cause the failure force limit to be lower. The smaller the apex angle α, the "sharper" the tip of the microneedle. However, by making the apex angle too small (e.g., below about 30 degrees), the resulting microneedle volume and mechanical strength may be reduced to an undesirable level.

The penetration force of a microneedle is inversely proportional to the microneedle sharpness, which is characterized not only by the included (apex) angle of the microneedles, but also by the radius of the microneedle tip. While the apex angle is prescribed by the mastermold geometry, the tip sharpness also depends on the reliability of the mold. Micromilling of mastermolds as described herein allows for increased accuracy in mold geometry which, in turn, results in an increased accuracy and reliability in the resulting production mold and the microneedle array formed by the production mold.

The increased accuracy of micromilling permits more accurate and detailed elements to be included in the mold design. For example, as discussed in the next section below, the formation of a fillet at the base of a pillar type microneedle can significantly increase the structural integrity of the microneedle, which reduces the likelihood that the microneedle will fail or break when it impacts the skin. While these fillets can significantly increase the strength of the microneedles, they do not interfere with the functional requirements of the microneedles (e.g., penetration depth and biologics volume). Such fillets are very small features that can be difficult to create in a master mold formed by conventional techniques. However, the micromilling techniques described above permit the inclusion of such small features with little or no difficulty.

Mechanical Integrity and Penetration Capabilities

Figure 7:
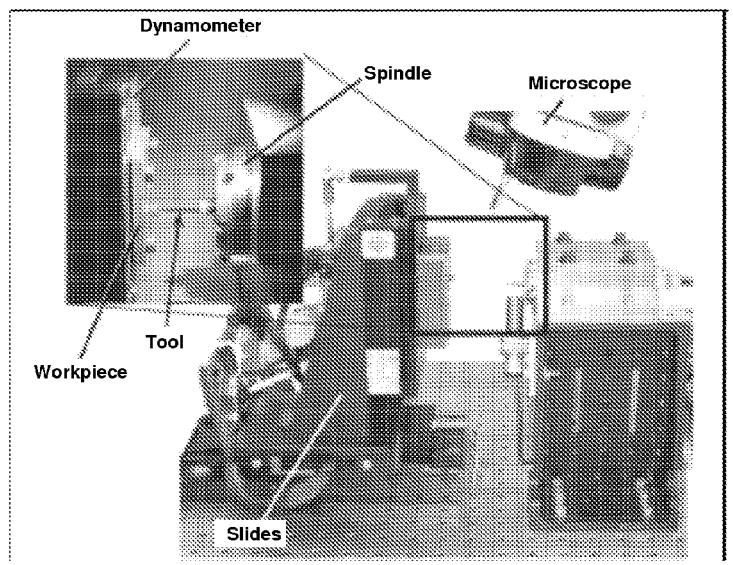
FIG. 7 illustrates a miniature precision-micromilling system used for fabricating microneedle mastermolds.

Microneedle arrays are preferably configured to penetrate the stratum corneum to deliver their cargo (e.g., biologics or bioactive components) to the epidermis and/or dermis, while minimizing pain and bleeding by preventing penetration to deeper layers that may contain nerve endings and vessels. To assess the mechanical viability of the fabricated microneedle arrays, tests were performed on the pyramidal and pillar type microneedle arrays as representative variants of array geometry (shown, e.g., in FIGS. 7B and 8). The first set of tests illustrate the failure limit of microneedles, and include pressing the microneedle array against a solid acrylic surface with a constant approach speed, while simultaneously measuring the force and the displacement until failure occurs. The second set of tests illustrate the piercing capability of the microneedles on human skin explants.

Figure 21:
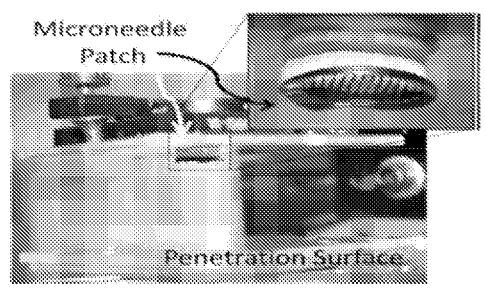
FIG. 21 illustrates a test apparatus for performing failure and piercing tests.

FIG. 21 illustrates a test apparatus designed for functional testing. The sample (i.e., microneedle array) was attached to a fixture, which was advanced toward a stationary acrylic artifact (PMMA surface) at a constant speed of about 10 mm/s speed using a computer-controlled motion stage (ES14283-52 Aerotech, Inc.). A tri-axial dynamometer (9256C1, Kistler, Inc.) that hosted the acrylic artifact enabled high-sensitivity measurement of the forces.

Figure 22:
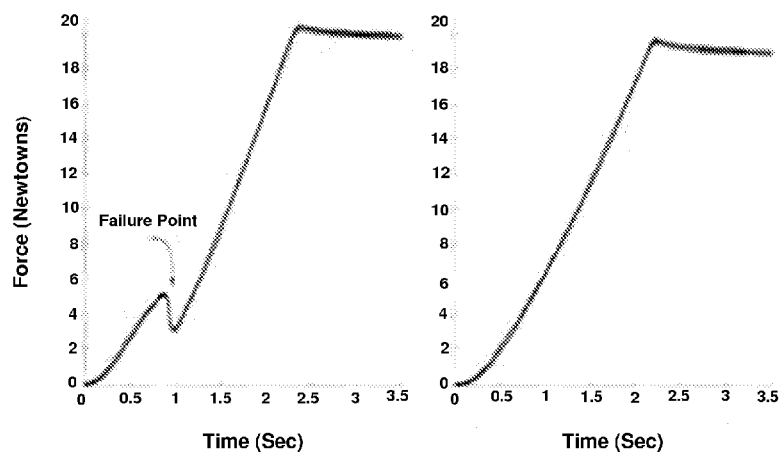
FIG. 22 illustrates force-displacement curves for pillar type microneedles (left) and pyramidal type microneedles (right).

FIG. 22 illustrates force-displacement curves of data measured during failure tests. The curve on the left is representative of data obtained from testing a pillar microneedle sample and the curve on the right is representative of data obtained from testing a pyramid microneedle. As seen in FIG. 22, the failure of these two kinds of microneedles are significantly different; while the pyramidal arrays plastically deform (bend), the pillar type arrays exhibit breakage of the pillars at their base. This different failure behavior lends itself to considerably different displacement-force data. The failure (breakage) event can be easily identified from the displacement-force data as indicated in the figure. Based on the obtained data, the failure point of pillar type microneedles was seen to be 100 mN in average. As only about 40 mN of force is required for penetration through the stratum corneum, the microneedles are strong enough to penetrate human skin without failure. Furthermore, since parallelism between microneedle tips and the acrylic artifact cannot be established perfectly, the actual failure limit will likely be significantly higher than 100 mN (i.e., microneedles broke in a successive manner, rather than simultaneous breakage of most/all microneedles).

The pyramidal microneedles presented a continuously increasing force signature with no clear indication of point of failure. To identify the failure limit for the pyramidal microneedles, interrupted tests were conducted in which the microneedles were advanced into the artifact by a certain amount, and retreated and examined through optical microscope images. This process was continued until failure was observed. For this purpose, the failure was defined as the bending of the pyramidal microneedles beyond 15 degrees.

Figure 23:
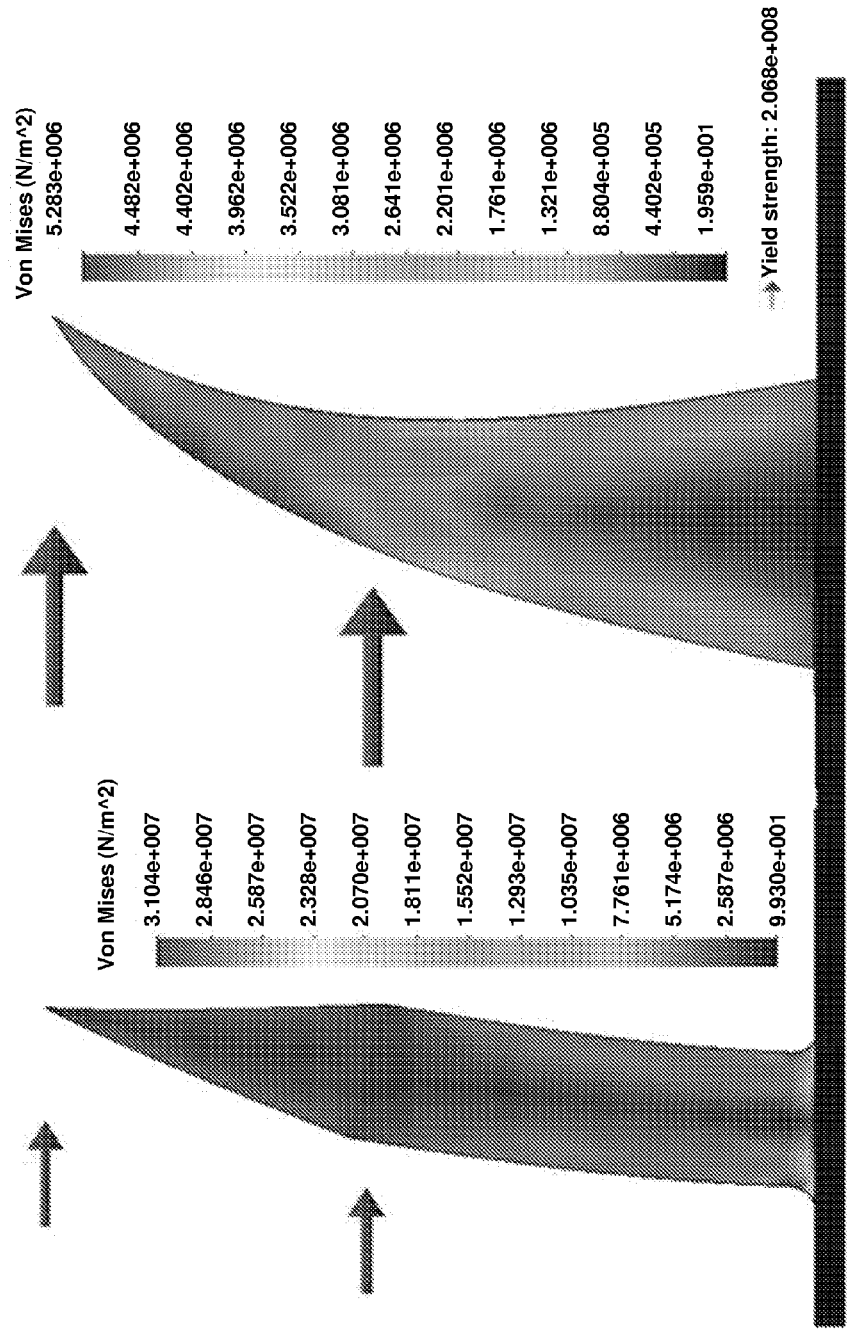
FIG. 23 illustrates a finite elements model of microneedle deflections for pillar type microneedles (left) and pyramidal type microneedles (right).
Figure 24A:
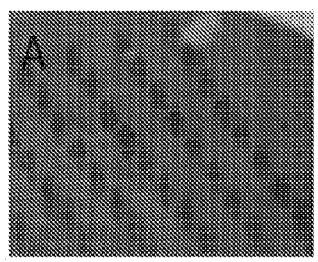
FIG. 24 show various stereo micrographs of the penetration of pyramidal (A, C, E) and pillar (B, D, F) type microneedles in skin explants.
Figure 24B:
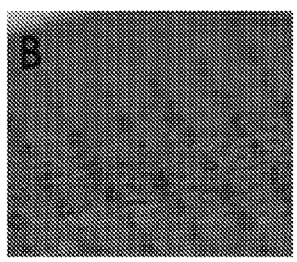
Figure 24C:
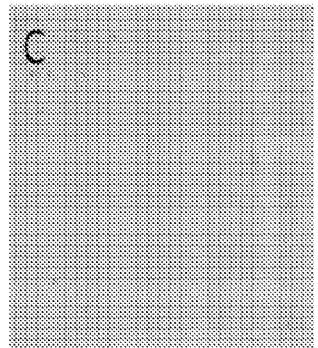
Figure 24D:
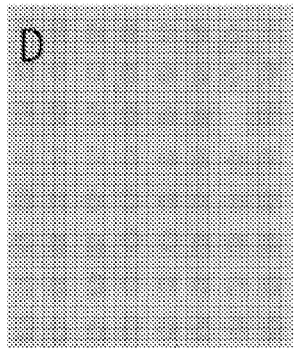
Figure 24E:
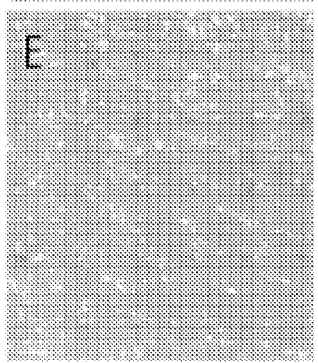
Figure 24F:
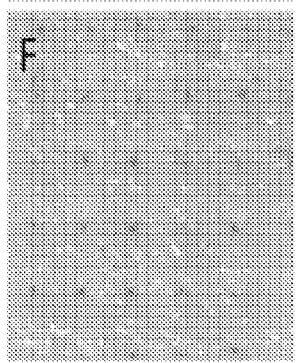
Figure 33:
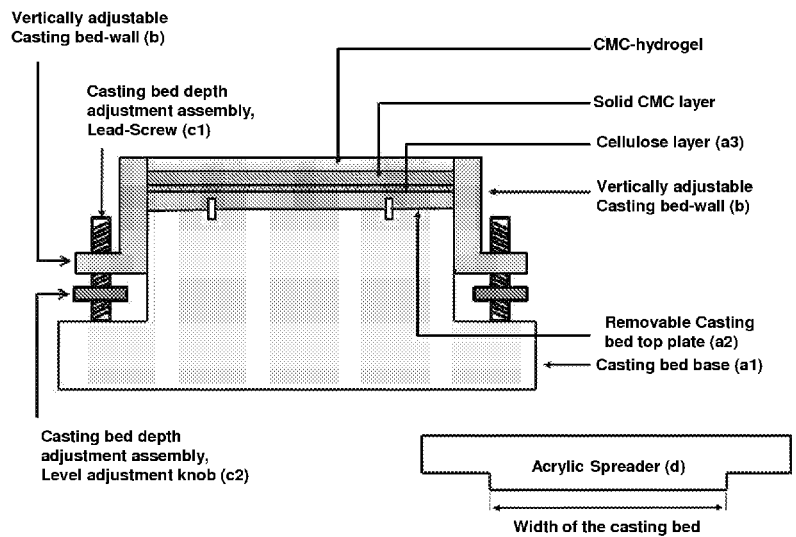
FIG. 33 is a schematic cross-sectional view of a casting-mold assembly for creating a block or sheet of material for direct micromilling.
Figure 34:
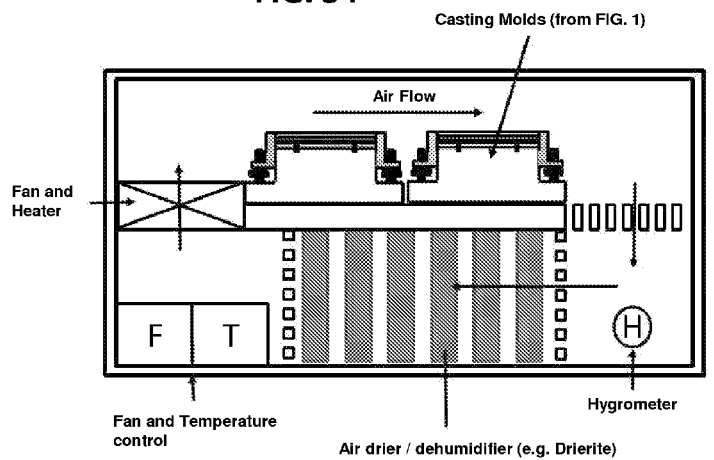
FIG. 34 is a schematic cross-sectional view of a drying apparatus that can be used to dry a block or sheet of material for direct micromilling.

To further analyze the failure of the microneedles, the finite-elements model (FEM) of the microneedle arrays shown in FIG. 23 was developed. To obtain the mechanical properties (elastic modulus and strength limit) of the CMC material, a series of nanoindentation tests (using a Hysitron nanoindentor). The average elastic modulus and yield strength of the CMC material (as prepared) were 10.8 GPa and 173 MPa, respectively. This indicates that the prepared CMC material has a higher elastic modulus and yield strength than both PMMA (elastic modulus: 3.1 GPa, yield strength: 103 MPa) and polycarbonate (elastic modulus: 2.2 GPa, yield strength: 75 MPa), indicating the superior strength and stiffness of CMC material with respect to other polymers.

Using this data, a series of FEM simulations were conducted. It was predicted from the FEM models that failure limit of pyramidal and sharp-pillar (width=134 μm) microneedles with 600 μm height, 30 degree apex angle, and 20 μm fillet radius were 400 mN (pyramid) and 290 mN (sharp-pillar) for asymmetric loading (5 degrees loading misorientation). Considering that the minimum piercing force requirement is about 40 mN, pyramid and sharp-pillar microneedles would have factors of safety of about 10 and 7.25, respectively.

When the fillet radius is doubled to 40 μm, the failure load for the pillar was increased to 350 mN, and when the fillet radius is reduced to 5 μm, the failure load was reduced to 160 mN, which is close to the experimentally determined failure load. The height and width of the pillars had a significant effect on failure load. For instance, for 100 μm width pillars, increasing the height from 500 μm to 1000 μm reduced the failure load from 230 mN to 150 mN. When the width is reduced to 75 μm, for a 750 μm high pillar, the failure load was seen to be 87 mN.

To evaluate penetration capability, pyramidal and sharp-pillar microneedle arrays were tested for piercing on water-based model elastic substrates and on full thickness human skin. FIG. 24 illustrates stereo micrographs of pyramidal (Panels A, C, and E) and pillar type microneedle arrays (B, D, and F) after 4 minutes of exposure to model elastics. In particular, toluene blue tracer dye was deposited in model elastic substrates (Panels C and D) or freshly excised full thickness human skin explants (Panels E and F) after application of pyramidal or pillar type microneedle arrays.

The model elastic substrate comprised about 10% CMC and about 10% porcine gelatin in PBS gelled at about 4 degrees Celsius for about 24 hours or longer. The surface of the elastics was covered with about 100 μm thick parafilm to prevent the immediate contact of the needle-tips and the patch materials with the water based model elastics. To enable stereo microscopic-imaging, trypan blue tracer dye (Sigma Chem., cat #T6146) was incorporated into the CMC-hydrogel at 0.1% concentration. The patches were applied using a spring-loaded applicator and analyzed after about a 4 minute exposure. Based on physical observation of the dye in the target substrates, the dissolution of the microneedles of the two different geometries was markedly different.

The sharp-pillar needles applied to the model elastic substrate released substantially more tracer dye to the gel matrix than that observed for the pyramidal design (FIG. 24, C vs. D). Images of the recovered patches (FIG. 24, A vs. B) were consistent with this observation, as the degradation of the sharp-pillar needles was more advanced than that of the pyramidal needles. To extrapolate this analysis to a more clinically relevant model, pyramidal and pillar type microneedle arrays were applied to freshly excised full thickness human skin explants using the same force from the spring loaded applicator. Consistent with results from the elastic model, the pyramidal microneedle arrays deposited visibly less tracer dye than the sharp-pillar microneedle arrays (FIG. 24, E vs. F).

To further evaluate penetration and to assess delivery effectiveness to human skin, CMC-microneedle arrays were fabricated with BioMag (Polysciences, Inc., cat#. 84100) beads or fluorescent particulate tracers (Fluoresbrite YG 1 μm, Polysciences Inc., cat#. 15702). The pyramidal CMC-microneedle arrays containing fluorescent or solid particulates were applied to living human skin explants as described previously. Five minutes after the application, surface residues were removed and skin samples were cryo-sectioned and then counterstained with toluene blue for imaging by light microscopy (FIGS. 25A and 25B) or by fluorescent microscopy (FIG. 25C).

Figure 40:
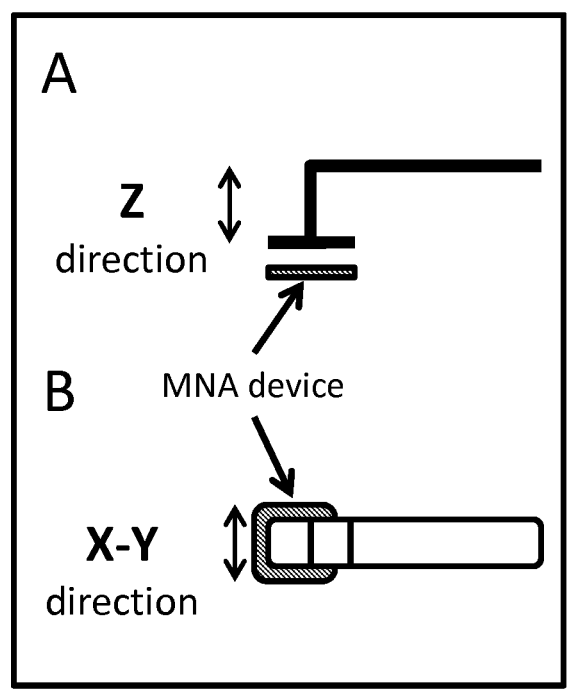
FIG. 40 is a schematic view of dimensional movement of an applicator head.

Pyramidal CMC-microneedles effectively penetrated the stratum corneum, epidermis, and dermis of living human skin explants, as evidenced by the deposition of Biomag beads lining penetration cavities corresponding to individual needle insertion points (representative sections shown in FIGS. 25A and 25B). In particular, ordered cavities (FIG. 25A, cavities numbered 1-4, toluene blue counterstain, 10×) and deposits of BioMag particles (brown) lining penetration cavities were evident (FIG. 25B, 40×), indicating microneedle penetrated of human skin. Further, analysis of sections from living human explants stained with DAPI to identify cell nuclei and anti-HLA-DR to identify MHC class II+ antigen presenting cells revealed high density fluorescent particulates deposited in the superficial epidermis and dermis, including several particles co-localized with class II+ antigen presenting cells (FIG. 25C, DAPI (blue), HLA-DR+ (red) and fluorescent particles (green), 40×).

These results further demonstrate that the CMC microneedle arrays described herein can effectively penetrate human skin and deliver integral cargo (bioactive components), including insoluble particulates. They are consistent with effective delivery of particulate antigens to antigen presenting cells in human skin, currently a major goal of rational vaccine design.

To further address microneedle array delivery in vivo, the cutaneous delivery of particulate antigen in vivo was modeled by similarly applying fluorescent particle containing arrays to the dorsal aspect of the ears of anesthetized mice. After 5 minutes, patches were removed and mice resumed their normal activity. Three hours or 3 days, ear skin and draining lymph nodes were analyzed for the presence of fluorescent particles. Consistent with observations of human skin, particulates were evident in the skin excised from the array application site (data not shown). Further, at the 3 day time point, substantial numbers of particles were evident in the draining lymph nodes. FIGS. 26A and 26B illustrates substantial numbers of particles that were evident in the draining lymph Nodes (FIG. 26A, 10×), including clusters of particulates closely associated with Class II+ cells (FIG. 26B, 60×) suggesting the presence of lymph node resident antigen presenting cells with internalized particulates.

To quantitatively evaluate the effects of needle geometry on cargo delivery using microneedle arrays, 3H-tracer labeled CMC-microneedle arrays were constructed. The CMC-hydrogel was prepared with 5% wt ovalbumin as a model active component at 25 wt % final dry weight content (5 g/95 g OVA/CMC) and trace labeled with 0.1 wt % trypan blue and 0.5×10⁶ dpm/mg dry weight 3H-tracer in the form of 3H-thymidine (ICN Inc., cat #2406005). From a single batch of labeled CMC-hydrogel-preparation four batches of 3H-CMC-microneedle arrays were fabricated, containing several individual patches of pyramidal and sharp-pillar needle geometry. The patches were applied to human skin explants as described above and removed after 30 min exposure. The patch-treated area was tape-striped to remove surface debris and cut using a 10 mm biopsy punch. The 3H content of the excised human skin explants-discs was determined by scintillation counting. The specific activity of the 3H-CMC-microneedle patch-material was determined and calculated to be 72,372 cpm/mg dry weight. This specific activity was used to indirectly determine the amount of ovalbumin delivered to and retained in the skin. The resulting data is summarized in Table 1 below.

The tested types of patches were consistent from microneedle array to microneedle array (average standard deviation 24-35%) and batch to batch (average standard deviation 7-19%). The intra-batch variability for both needle geometry was lower than the in-batch value indicating that the insertion process and the characteristics of the target likely plays a primary role in the successful transdermal material delivery and retention. The patch-material retention data clearly demonstrate the foremost importance of the microneedle geometry in transdermal cargo delivery. Pillar-type needle geometry afforded an overall 3.89 fold greater deposition of the 3H labeled needle material than that of the pyramidal needles. On the basis of the deposited radioactive material, it is estimated that the pyramidal needles were inserted about 200 μm deep while the pillar-type were inserted about 400 μm or more.

TABLE 4.2.5

Transfer of ³H-labeled CMC-microneedle material into human skin explants by pyramidal and pillar-type needles.

| Array Batches | Pyramid Needles (cpm/patch) | STDev (%) | Pyramidal Needles OVA Transferred (μg/patch) | Pillar-Type Needles (cpm/patch) | STDev (%) | Pillar-Type Needles OVA Transferred (μg/patch) | Pillar to Pyramid Ratio |
|---|---|---|---|---|---|---|---|
| Batch A | 2459.00 | 17.56 | 1.70 | 11700.50 | 31.52 | 8.08 | 4.76 |
| Batch B | 3273.50 | 57.39 | 2.26 | 12816.50 | 21.45 | 8.85 | 3.92 |
| Batch C | 2757.75 | 46.13 | 1.90 | 12240.00 | 26.77 | 8.46 | 4.44 |
| Batch D | 3782.00 | 36.27 | 2.61 | 10921.50 | 9.32 | 7.55 | 2.89 |
| IntraBatch AVG | 3068.06 | 19.00 | 2.12 | 11919.63 | 6.77 | 8.24 | 3.89 |

Desirably, the microneedle arrays described herein can be used for cutaneous immunization. The development of strategies for effective delivery of antigens and adjuvants is a major goal of vaccine design, and immunization strategies targeting cutaneous dendritic cells have various advantages over traditional vaccines.

The microneedle arrays described herein can also be effective in chemotherapy and immunochemotherapy applications. Effective and specific delivery of chemotherapeutic agents to tumors, including skin tumors is a major goal of modern tumor therapy. However, systemic delivery of chemotherapeutic agents is limited by multiple well-established toxicities. In the case of cutaneous tumors, including skin derived tumors (such as basal cell, squamous cell, Merkel cell, and melanomas) and tumors metastatic to skin (such as breast cancer, melanoma), topical delivery can be effective. Current methods of topical delivery generally require the application of creams or repeated local injections. The effectiveness of these approaches is currently limited by limited penetration of active agents into the skin, non-specificity, and unwanted side effects.

The microneedle arrays of the present disclosure can be used as an alternative to or in addition to traditional topical chemotherapy approaches. The microneedle arrays of the present disclosure can penetrate the outer layers of the skin and effectively deliver the active biologic to living cells in the dermis and epidermis. Delivery of a chemotherapeutic agents results in the apoptosis and death of skin cells.

Further, multiple bioactive agents can be delivered in a single microneedle array (patch). This enables an immunochemotherapeutic approach based on the co-delivery of a cytotoxic agent with and immune stimulant (adjuvants). In an immunogenic environment created by the adjuvant, tumor antigens releases from dying tumor cells will be presented to the immune system, inducing a local and systemic anti-tumor immune response capable of rejecting tumor cells at the site of the treatment and throughout the body.

In an exemplary embodiment, the delivery of a biologically active small molecule was studied. In particular, the activity of the chemotherapeutic agent Cytoxan® delivered to the skin with CMC microneedle arrays was studied. The use of Cytoxan® enables direct measurement of biologic activity (Cytoxan® induced apoptosis in the skin) with a representative of a class of agents with potential clinical utility for the localized treatment of a range of cutaneous malignancies.

To directly evaluate the immunogenicity of CMC microneedle array incorporated antigens, the well characterized model antigen ovalbumin was used. Pyramidal arrays were fabricated incorporating either soluble ovalbumin (sOVA), particulate ovalbumin (pOVA), or arrays containing both pOVA along with CpGs. The adjuvant effects of CpGs are well characterized in animal models, and their adjuvanticity in humans is currently being evaluated in clinical trials.

Immunization was achieved by applying antigen containing CMC-microneedle arrays to the ears of anesthetized mice using a spring-loaded applicator as described above, followed by removal of the arrays 5 minutes after application. These pyramidal microneedle arrays contained about 5 wt % OVA in CMC and about 0.075 wt % (20 μM) CpG. As a positive control, gene gun based genetic immunization strategy using plasmid DNA encoding OVA was used. Gene gun immunization is among the most potent and reproducible methods for the induction of CTL mediated immune responses in murine models, suggesting its use as a "gold standard" for comparison in these assays.

Mice were immunized, boosted one week later, and then assayed for OVA-specific CTL activity in vivo. Notably, immunization with arrays containing small quantities of OVA and CpG induced high levels of CTL activity, similar to those observed by gene gun immunization (FIG. 27). Significant OVA-specific CTL activity was elicited even in the absence of adjuvant, both with particulate and soluble array delivered OVA antigen. It is well established that similar responses require substantially higher doses of antigen when delivered by traditional needle injection.

To evaluate the stability of fabricated arrays, batches of arrays were fabricated, stored, and then used over an extended period of time. As shown in FIG. 28, no significant deterioration of immunogenicity was observed over storage periods spanning up to 80 days (longest time point evaluated). Thus, the CMC microneedle arrays and this delivery technology can enable effective cutaneous delivery of antigen and adjuvants to elicit antigen specific immunity.

To evaluate the delivery of a biologically active small molecule, pyramidal CMC-microneedle arrays were fabricated with the low molecular weight chemotherapeutic agent Cytoxan® (cyclophosphamide), or with FluoresBrite green fluorescent particles as a control. Cytoxan® was integrated at a concentration of 5 mg/g of CMC, enabling delivery of approximately about 140 μg per array. This is a therapeutically relevant concentration based on the area of skin targeted, yet well below levels associated with systemic toxicities. Living human skin organ cultures were used to assess the cytotoxicty of Cytoxan®. Cytoxan® was delivered by application of arrays to skin explants as we previously described. Arrays and residual material were removed 5 minutes after application, and after 72 hours of exposure, culture living skin explants were cryo-sectioned and fixed. Apoptosis was evaluated using green fluorescent TUNEL assay (In Situ Cell Death Detection Kit, TMR Green, Roche, cat#:11-684-795-910). Fluorescent microscopic image analysis of the human skin sections revealed extensive apoptosis of epidermal cells in Cytoxan® treated skin as shown in FIG. 29A. As shown in FIG. 29B, no visible apoptosis was observed in fluorescent particle treated skin though these particles were evident, validating that the observed area was accurately targeted by the microneedle array.

Direct Fabricated Microneedle Arrays

The micromilling of mastermolds described above allows the production of microneedle arrays with a variety of geometries. In another embodiment, systems and methods are provided for fabricating a microneedle array by directly micromilling various materials, such as dried CMC sheets. The same general tooling that was described above with respect to the micromilling of mastermolds can be used to directly micromill microneedle arrays.

Direct micromilling of microneedle arrays eliminates the need for molding steps and enables a simplified, scalable, and precisely reproducible production strategy that will be compatible with large scale clinical use. Moreover, direct fabrication of the microneedle arrays through micromilling enables greater control of microneedle geometries. For example, micromilling permits the inclusion of microneedle retaining features such as undercuts and/or bevels, which cannot be achieved using molding processes.

The reproducibility of direct milling of microneedle arrays is particular beneficial. That is, in direct micromilling all of the microneedles are identical as a result of the milling fabrication process. In molding operations, it is not uncommon for some needles to be missing or broken from a given patch as a result of the process of physically separating them from the molds. For use in certain medical applications, the reproducibility of the amount of bioactive components in the array is very important to provide an appropriate level of "quality control" over the process, since irregularities in the needles from patch to patch would likely result in variability in the dose of drug/vaccine delivered. Of course, reproducibility will also be an important benefit to any application that requires FDA approval. Spincast/molded patches would require special processes to assure acceptable uniformity for consistent drug delivery. This quality control would also be likely to result in a certain percentage of the patches "failing" this release test, introducing waste into the production process. Direct micromilling eliminates or at least significantly reduces these potential problems.

Molding processes also have inherent limitations because of the need to be able to fill a well or concavity and remove the cured molded part from that well or concavity. That is because of mold geometries, undercuts must generally be avoided when molding parts or the part will not be removable from the mold. That is, a geometrical limitation of a molded part, such as a molded microneedle array, is that any feature located closer to the apex must be narrower than any feature located toward the base.

Accordingly, in view of these limitations, FIG. 20 illustrates schematic representation of microneedle shapes and structures that are generally suitable for fabrication by molding. That is, the shapes and structures shown in FIG. 20 do not contain any undercuts that would prevent the part (i.e., the microneedles) from being removed from a production mold. In contrast, FIG. 30 illustrates a beveled, undercut microneedle shape that cannot be molded in the manners described herein.

This geometry can only be created through direct fabrication using the proposed micromilling technology. The negative (bevel) angle facilitates better retention of the microneedles in the tissue. In addition, because the microneedle of FIG. 30 has a wider intermediate portion (with a larger cross-sectional dimension) above a lower portion (with a smaller cross-sectional dimension), a greater amount of the bioactive material can be delivered by configuring the microneedle to hold or store the bioactive material in the wider section, which is configured to be retained within the skin. Thus, the larger cross-sectional dimension of the intermediate portion can "carry" the bulk of the bioactive component. Since the lower portion tapers to a narrower cross-sectional dimension, the wider intermediate portion will obtain good penetration for delivery of the bioactive component into the skin layer. A portion above the intermediate portion desirably narrows to a point to facilitate entry of the microneedles into the skin layers.

Another limitation of molded parts is that it can be difficult to precisely fill a very small section of a mold. Since production molds for microneedle arrays comprise numerous very small sections, it can be difficult to accurately fill each well. This can be particularly problematic when the mold must be filled with different materials, such as a material that contains a bioactive component and a material that does not contain a bioactive component. Thus, if the production mold is to be filled with layers, it can be difficult to accurately fill the tiny wells that are associated with each microneedle. Such reproducibility is particularly important, since the microneedles are intended to deliver one or more bioactive components. Thus, even slight variations in the amounts of bioactive component used to fill production molds can be very undesirable.

Also, by using a lamination structure to form a sheet or block that can be micromilled, various active components can be integrated into a single microneedle by vertical layering. For example, in an exemplary embodiment, CMC-hydrogel and CMC-sOVA-hydrogel (80% CMC/20 wt % OVA) were layered into the form of a sheet or block. This composite sheet can be micro-machined using the direct micromilling techniques described herein.

FIG. 31 is a stereo-microscopic image analysis of an entire microneedle array. The microneedle comprises a 10×10 array of microneedles. FIG. 32 is an enlarged segment of the microneedle array of FIG. 31. The layering of two components is shown in FIG. 32, which illustrates darker areas of the microneedles at tip portions and lighter areas of the microneedles at base portions. The darker layer at the tip represents the layer comprising a bioactive component, in this case soluble ovalbumin contained in a CMC layer.

Although the formation of a layer containing active material (e.g., antigen) and the subsequent micromilling of the layer (and any other adjacent layers) may require the use of relatively large amounts of the active material, the material can be removed (e.g., in the form of chips), recovered, and recycled. Direct machining technology is not restricted by the geometrical constraints arising from the molding/demolding approach, and thus, is capable of creating more innovative needle designs (e.g., FIG. 30), which can significantly improve the retained needle-volume and needle retention time in the skin.

The production of sheets or blocks by forming a plurality of layers can provide a solid material that can be micro-machined and which can comprise one or more layers with a bioactive component. For example, a dissolvable solid carboxymethylcellulose polymer based block or sheet with well-defined and controlled dimensions can be fabricated by a lamination process. The resulting sheet or block can be fully machineable, similar to the machining of plastic or metal sheets or blocks. As described herein, the fabrication process can be suitable for the incorporation of bioactive components into the matrix without significantly reducing their activity levels.

As described below, a fabricated sheet of material (such as a CMC based material) can be directly micro-machined/micromilled) to produce one or more microneedle arrays suitable for delivering active ingredients through the skin. This dissoluble biocompatible CMC block-material can be used for the delivery of soluble or insoluble and particulate agents in a time release manner for body surface application. The biocompatible material can be suitable for implants in deeper soft or hard tissue when dissolution of the scaffolding material is required and useful.

The following method can be used to prepare a carboxymethylcellulose (CMC) polymer low viscosity hydrogel to 12.5% concentration. The 12.5% carboxymethylcellulose (CMC) low viscosity hydrogel can be prepared in water or other biocompatible buffer, such as (but not limited to) PBS or HBS. During the preparation of the polymer solution, soluble agents (such as nucleic acid, peptides, proteins, lipids or other organic and inorganic biologically active components) and particulates can be added (e.g. ovalbumin, a soluble agent). Ferrous particulates carrying active ingredients at 20 w/w % of CMC can be used.

The preparation of 1000 g sterile 12.5% CMC hydrogel with no active component can be achieved as follows:

1) Measure 125 g CMC, add 875 g water or other water based solvent.
2) Stir to homogeneity in overhead mixer.
3) Autoclave homogenate to sterility at 121 degrees Celsius for 1 hour (the autoclaving step can reduce viscosity for improved layering)
4) Cool to 22 degrees Celsius.
5) Vacuum treat the resulting material at 10 torr and 22 degrees Celsius for 1 hour to remove trapped micro-bubbles.
6) Centrifuge product at 25,000 g for 1 hour in vacuum chambered centrifuge (for floating and further removing residual micro bubbles).
7) Store the CMC-hydrogel product at 4 degrees Celsius.

The preparation of 1000 g sterile 12.5 w/w % dry content 20/80% ovalbumin/CMC hydrogel can be achieved as follows:

1) Measure 100 g CMC add 650 g water or other water based solvent.
2) Stir to homogeneity in overhead mixer.
3) Autoclave homogenate to sterility at 121 degrees Celsius for 1 hour (this autoclaving step can reduce viscosity for improved layering).
4) Cool to 22 degrees Celsius.
5a) Dissolve 25 g ovalbumin in 225 g water.
5b) Sterile filter ovalbumin solution on 0.22 μm pore sized filter.
6) Mix to homogeneity, under sterile conditions the 750 g CMC hydrogel with 250 g sterile ovalbumin solution.
7) Vacuum treat the resulting material at 10 torr and 22 degrees Celsius for 1 hour to remove trapped micro-bubbles.
8) Centrifuge product at 25,000 g for 1 hour in vacuum chambered centrifuge (for floating and further removing residual micro bubbles).
9) Store the CMC-hydrogel product at 4 degrees Celsius.

The preparation of 100 g sterile 12.5 w/w % dry content 20/80% particulate-ovalbumin/CMC hydrogel can be achieved as follows:

1) Measure 10 g CMC add 87.5 g water or other water based solvent.
2) Stir to homogeneity in overhead mixer.
3) Autoclave homogenate to sterility at 121 degrees Celsius for 1 hour (this autoclaving step can reduce viscosity for improved layering).
4) Cool to 22 degrees Celsius.
5) Disperse 2.5 g particulate-ovalbumin in the 97.5 g, 22 degrees Celsius CMC-hydrogel and mix to homogeneity, under sterile conditions.

6) Vacuum treat the resulting material at 10 torr and 22 degrees Celsius for 2 hour to remove trapped micro-bubbles.

7) Centrifuge product at 3,000 g for 1 hour in vacuum chambered centrifuge (for floating and further removing residual micro bubbles).

8) Store the CMC-hydrogel product at 4 degrees Celsius.

Note in this example, particulate-ovalbumin is prepared from activated iron beads reaction to ovalbumin. However, it should be noted that the above descriptions are only exemplary embodiments and other compounds and active ingredients can be used.

A solid block/sheet carboxymethylcellulose (CMC) can be fabricated in the following manner using the low viscosity CMC-hydrogels described above.

The fabrication process can comprise a laminar spreading of the polymer at a defined thickness and a drying of the layered polymer to less than about 5% water content using sterile dried air flow over the surface of the polymer layer. The above two acts can repeated until the desired block thickness is achieved.

A method of performing a laminar CMC-hydrogel layering of a defined thickness over the casting mold assembly is described with reference to FIG. 33. FIG. 33 illustrates a cross-sectional view of the casting-mold assembly which includes: (a) casting bed; (b) adjustable casting bed wall; (c) casting-bed depth adjustment assembly; and (d) an acrylic spreader. It should be noted that FIG. 33 is not drawn to scale or otherwise shown with elements in their proper proportions.

The casting mold assembly can be constructed from acrylic (Plexiglas) and can comprise a casting bed base unit, a vertically adjustable hydrophobic casting-bed wall, and a casting-bed adjustment mechanism. The casting bed base unit (a1) can include a removable/replaceable casting bed top plate (a2) with an attached cellulose layer (a3). The cellulose layer can be about 0.5 mm in thickness. The vertically adjustable hydrophobic casting-bed wall (b) can be adjusted using the casting-bed depth adjustment mechanism, which can be comprised of lead-screw (c1) and level adjustment knob (c2). In the illustrated embodiment, a quarter turn of this knob can result in a 0.5 mm lift of the bed wall.

Initially, the adjustable casting bed wall can be set to height where the distance between the acrylic spreader and the cellulose layer of the bed is about 1 mm when the spreader is in position. A predefined volume (e.g., about 0.1 ml/cm2) of the 12.5% CMC-hydrogel can be added and layered. The layer can be evened or leveled by sliding the acrylic spreader (d) on the top surface of the adjustable casting wall to yield an even layer of about 1 mm of CMC-hydrogel. The layered CMC-hydrogel can be dried to a solid phase in the drying apparatus shown in FIG. 34 and described in more detail below.

The layering and drying steps can be repeated until the desired layered structure (sheet) is achieved. The casting bed wall can be raised by an appropriate amount during the addition of each layer. For example, after adding each layer, the bed wall can be raised or lifted by about 0.5 mm. Thus, the above-described cycle can deposit about 0.5 mm solid CMC layer. The process (e.g., the layering of material, the raising of bed wall, etc.) can be repeated until the desired block thickness achieved.

The layered CMC-hydrogel polymer can be dried in various manners. For example, FIG. 34 illustrates a drying apparatus that can be used to dry the various deposited layers of the sheet material. It should be noted that FIG. 34 is not drawn to scale or otherwise shown with elements in their proper proportions. A fan can provide continuous gas flow (e.g., air or other inert gas, such as nitrogen) over the CMC-hydrogel layered in the casting mold assembly. The gas flow will result in a gentle dehydration of the CMC-hydrogel layer. The drying speed can be adjusted to prevent or reduce gas enclosures (e.g., air bubbles) in the solid CMC product. The humid air over the layer can be dried over desiccant (e.g., an air dryer or dehumidifier), temperature adjusted, and returned over the hydrogel again by the speed-controlled fan. A hygrometer can be positioned on the humid side of the chamber to provide an indication of the status of the drying process. After a predetermined dryness has been achieved, as indicated by the hygrometer, the drying process can be ended.

Airflow can be adjusted to affect the drying speed. In the exemplary embodiment, the airflow is controlled to be between about 0.1-2.0 m/sec; the temperature is between ambient and about 50 degrees Celsius. Using these configurations, the drying time of a single layer CMC-hydrogel can be about 0.5-4 hours depend on the airflow and the set temperature.

The pure CMC based product can be transparent, light off white, or amber colored. Its specific gravity can be about 1.55-1.58 g/ml. The product is desirably free of micro-bubbles and otherwise suitable for fabricating micron scale objects. The physical characterization of the final block/sheet product (hardness, tensile strength, etc.) can vary, but should generally be able to resist physical stresses associated with micromilling.

As described above, the microneedle arrays disclosed herein are capable of providing reliable and accurate delivery methods for various bioactive components. The structural, manufacturing, and distribution advantages characteristic of the above-described microneedle arrays can be particularly applicable for use in delivering vaccines. Advantages of these microneedle arrays include (1) safety, obviating the use of needles or living vectors for vaccine delivery, (2) economy, due to inexpensive production, product stability, and ease of distribution, and 3) diversity, via a delivery platform compatible with diverse antigen and adjuvant formulations.

Moreover, cutaneous immunization by microneedle array has important advantages in immunogenicity. The skin is rich in readily accessible dendritic cells (DCs), and has long been regarded as a highly immunogenic target for vaccine delivery. These dendritic cell populations constitute the most powerful antigen presenting cells (APCs) identified thus far. For example, genetic immunization of skin results in transfection and activation of dendritic cells in murine and human skin, and these transfected dendritic cells synthesize transgenic antigens, migrate to skin draining lymph nodes, and efficiently present them through the MHC class I restricted pathway to stimulate CD8+ T-cells. The immune responses induced by skin derived DCs are remarkably potent and long-lasting compared to those induced by other immunization approaches. Recent clinical studies demonstrate that even conventional vaccines are significantly more potent when delivered intradermally, rather than by standard intramuscular needle injection. Thus, microneedle arrays can efficiently and simultaneously deliver both antigens and adjuvants, enabling both the targeting of DCs and adjuvant engineering of the immune response using the same delivery platform.

High Frequency Electro-magnetic Oscillating Applicator

Microneedle array devices can be applied to human skin by a variety of methods including self or assisted application by human pressure (e.g., pushing with a finger or thumb), or with spring-loaded devices. To facilitate the ease and reproducibility of delivery of microneedle array devices, including tip-loaded microneedle arrays, an applicator device is described herein. The applicator device is configured to convert high frequency electromagnetic oscillation into unidirectional mechanical resonance of the active head. This in turn enables multiple reproducible low amplitude and high frequency pressure strokes that facilitate insertion of the microneedles of microneedle arrays into tissues including human skin.

Figure 38:
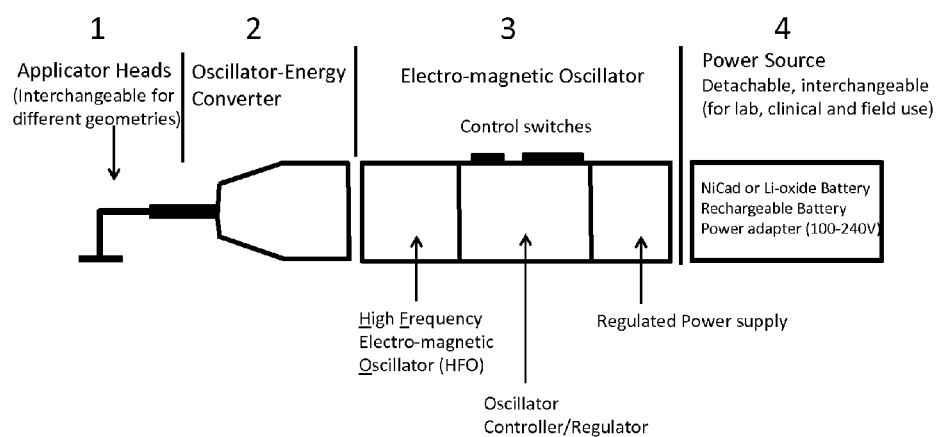
FIG. 38 illustrates an applicator for microneedle insertion into target tissue.

As shown in FIG. 38, the applicator can comprise an applicator head, an oscillator-energy converter, an electromagnetic oscillator, and a power source. If desired, one, or all of these four elements can be detachable from the applicator device.

Figure 39:
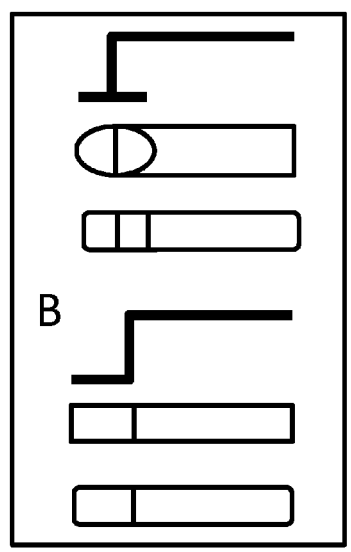
FIG. 39 illustrates applicator head designs for use with the applicator shown in FIG. 38.

An applicator head can be interchangeable to accommodate and act on different sized and shaped tissue surface areas. As shown in FIG. 39, various applicator head geometries can be utilized in combination with the applicator described herein. Applicator heads are interchangeable made of stainless steel or other chemically and physically resistant materials. If desired, the applicator heads can be autoclaved for sterility and/or sterilized by alcohols or other chemicals. Alternatively, or in addition, gas sterilization (ethylene oxide) is possible.

Application specific geometries can be rapidly designed and fabricated. For example, the area of a single application in this example can range from 5 mm$^2$ to 250 mm$^2$ dependent on the active head's geometry. A broader range can be achieved by simple structural variation of the head's geometry.

The oscillator energy converter unit can be configured to transforms the electro-magnetic oscillation into mechanical movements of the applicator head. The amplitude of the applicator head's in direction Z can be controlled between 0.5-2.5 mm (FIG. 40; A). In some embodiments, head movements in direction X-Y can be configured to be negligible, <0.2 mm (FIG. 40; B). The frequency of the mechanical movements resulting from the energy conversion in the direction Z can be controlled between 500-25000 rpm. If desired, the oscillator energy converter unit can be detachable and can be disposed or sterilized as needed.

The electro-magnetic (EM) oscillator can be composed of three subunits. These subunits can include a (1) regulated power supply generating the voltage and power for the controller and high frequency EM oscillator; a (2) controller-regulator generates the high frequency signal and the required current for the EM oscillator; and (3) an EM oscillator. The output frequency can be controlled by the user (e.g., in ranges such as from 100-500 Hz). In some embodiments, the EM oscillator can be fully enclosed and can be sterilized by alcohol solutions or other chemical agents.

The power source unit can also be detachable to accommodate different attachable power sources such as:
 a. Battery, regular disposable alkaline or any other type.
 b. Rechargeable NiCad or Li oxide battery with built in inductive charger.
 c. Electronic power adapter to 100-240 V The applicator can provide several benefits in connection with microneedle array application. For example, the applicator can minimalize the mechanical force needed for microneedle array insertion into tissues. The applicator can also reduce pain effects compared to existing spring-loaded applicators. In addition, the applicator can be portable and the components of the applicator can be detachable and interchangeable. Finally, the applicator can be configured so that it is capable of being sterilized for aseptic use.

In view of the many possible embodiments to which the principles of the disclosed embodiments may be applied, it should be recognized that the illustrated embodiments are only preferred examples and should not be taken as limiting the scope of protection. Rather, the scope of the protection is defined by the following claims. We therefore claim all that comes within the scope and spirit of these claims.

We claim:

1. A dissolvable microneedle array for transdermal insertion into a patient comprising:
 one or more bioactive components;
 a base portion; and
 a plurality of microneedles extending from the base portion, the plurality of microneedles comprising a top half and a bottom half
 wherein the one or more bioactive components are concentrated in the top half of the microneedles,
 wherein the base portion and the plurality of microneedles comprise a plurality of layers of dissolvable biocompatible material,
 wherein the dissoluble biocompatible material define a shape of the plurality of microneedles, the one or more bioactive components are contained in the plurality of layers, and at least some of the plurality of layers that contain the one or more bioactive components are spatially separated from others of the plurality of layers that contain the one or more bioactive components.

2. The dissolvable microneedle array of claim 1, wherein the base portion is substantially formed without any bioactive components contained therein.

3. The dissolvable microneedle array of claim 2, wherein the plurality of microneedles have a first cross-sectional dimension at an area of a top portion, a second cross-sectional dimension at an area of a bottom portion, and a third cross-sectional dimension at an area of an intermediate portion, wherein the third cross-sectional dimension is greater than the first and second cross-sectional dimensions.

4. The dissolvable microneedle array of claim 3, wherein each microneedle generally tapers to a point above the intermediate portion and each microneedle generally tapers to a smaller cross-sectional dimension below the intermediate portion.

5. The dissolvable microneedle array of claim 1, wherein the dissoluble biocompatible material is carboxymethylcellulose.

6. The dissolvable microneedle array of claim 2, wherein the one or more bioactive component comprises at least two different bioactive components.

7. The dissolvable microneedle array of claim 6, wherein the at least two different bioactive components are selected from the group consisting of a chemotherapeutic agent, an adjuvant, and a chemo attractant for a cancer chemo immunotherapy application.

8. The dissolvable microneedle array of claim 6, wherein the one or more bioactive component comprises an antigen and an adjuvant for a vaccine application.

9. The dissolvable microneedle array of claim 2, wherein the one or more bioactive component comprises at least one viral vector.

10. The dissolvable microneedle array of claim 9, wherein the at least one viral vector comprises an adenovector.

11. The dissolvable microneedle array of claim 1, wherein the one or more bioactive component comprises doxorubicin.

12. The dissolvable microneedle array of claim 1, wherein the spatially separated layers of the one or more bioactive components comprise different active components.

13. The dissolvable microneedle array of claim 1, wherein the spatially separated layers of the one or more bioactive components comprise different amounts of the same bioactive component.

14. The dissolvable microneedle array of claim 1, wherein the spatially separated layers of the one or more bioactive components comprise different concentrations of the same bioactive component.

* * * * *

UNITED STATES PATENT AND TRADEMARK OFFICE
CERTIFICATE OF CORRECTION

| | | |
|---|---|---|
| PATENT NO. | : 9,944,019 B2 | Page 1 of 1 |
| APPLICATION NO. | : 14/398375 | |
| DATED | : April 17, 2018 | |
| INVENTOR(S) | : Falo, Jr. et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 65 days.

Signed and Sealed this
Eighteenth Day of December, 2018

Andrei Iancu
*Director of the United States Patent and Trademark Office*